US008973784B2

(12) United States Patent
Lu et al.

(10) Patent No.: US 8,973,784 B2
(45) Date of Patent: Mar. 10, 2015

(54) DISPENSING DEVICE

(75) Inventors: Winston Lu, Kitchener (CA); Robert Morton, London (CA); Joaquim Balles, London (CA)

(73) Assignee: Trudell Medical International, London (CA)

( * ) Notice: Subject to any disclaimer, the term of this patent is extended or adjusted under 35 U.S.C. 154(b) by 1226 days.

(21) Appl. No.: 12/322,110

(22) Filed: Jan. 29, 2009

(65) Prior Publication Data

US 2009/0139518 A1 Jun. 4, 2009

Related U.S. Application Data

(63) Continuation of application No. 11/334,940, filed on Jan. 19, 2006, now Pat. No. 7,886,934.

(60) Provisional application No. 60/671,220, filed on Apr. 14, 2005, provisional application No. 60/645,095, filed on Jan. 20, 2005.

(51) Int. Cl.
*B67D 7/22* (2010.01)
*A61M 15/00* (2006.01)
*A61M 11/08* (2006.01)
*A61M 39/26* (2006.01)

(52) U.S. Cl.
CPC ............ *A61M 15/009* (2013.01); *A61M 11/08* (2013.01); *A61M 15/0065* (2013.01); *A61M 15/0021* (2014.02); *A61M 15/0068* (2014.02); *A61M 15/007* (2014.02); *A61M 15/0076* (2014.02); *A61M 15/008* (2014.02); *A61M 2039/268* (2013.01); *A61M 2205/27* (2013.01)

USPC ........................................ 222/36; 128/200.23

(58) Field of Classification Search
CPC ............ A61M 15/009; A61M 15/007; A61M 15/0065; A61M 15/0068; A61M 15/008; A61M 2039/268; A61M 2205/27
USPC .............. 222/36, 38, 48; 128/200.23, 205.15, 128/205.23, 203.15; 215/230
See application file for complete search history.

(56) References Cited

U.S. PATENT DOCUMENTS

| 152,980 A | 7/1874 | Donkin |
| 165,054 A | 6/1875 | Baldwin |

(Continued)

FOREIGN PATENT DOCUMENTS

| AU | 598250 B2 | 6/1990 |
| CA | 535518 | 1/1957 |

(Continued)

OTHER PUBLICATIONS

International Search Report in International Application No. PCT/IB2006/000084, dated Jun. 2, 2006, 9 pages.

(Continued)

*Primary Examiner* — Lien Ngo
(74) *Attorney, Agent, or Firm* — Brinks Gilson & Lione

(57) ABSTRACT

A system of medicament dispensers includes a plurality of dispenser housings each having a unique first indicia and a plurality of containers each having a unique second indicia. The unique second indicia of each of the containers corresponds to one of the unique first indicia of a corresponding one of the dispenser housings. Methods for associating various containers and dispensers is also provided.

30 Claims, 9 Drawing Sheets

(56) References Cited

U.S. PATENT DOCUMENTS

| | | |
|---|---|---|
| 385,256 A | 6/1888 | Eggers |
| 498,851 A | 6/1893 | Jones |
| 1,219,858 A | 3/1917 | Patterson |
| 2,455,962 A | 12/1948 | Wheeler et al. |
| 2,580,292 A | 12/1951 | Geary et al. |
| 2,587,147 A | 2/1952 | Guion et al. |
| 2,630,027 A | 3/1953 | Wunderlich |
| 2,644,452 A | 7/1953 | Brown |
| 2,767,680 A | 10/1956 | Lermer |
| 2,770,711 A | 11/1956 | Baranowski |
| 2,841,190 A | 7/1958 | Sheck |
| 2,883,086 A | 4/1959 | Davison et al. |
| 2,939,597 A | 6/1960 | Greene |
| 2,943,730 A | 7/1960 | Tregilgas |
| 2,953,242 A | 9/1960 | Shaw |
| 3,001,524 A | 9/1961 | Maison et al. |
| 3,073,468 A | 1/1963 | Arneson |
| 3,085,745 A | 4/1963 | Auberger |
| 3,119,557 A | 1/1964 | Chapman |
| 3,120,318 A | 2/1964 | Rigor |
| 3,148,801 A | 9/1964 | Radeloff et al. |
| 3,151,599 A | 10/1964 | Livingston |
| 3,170,597 A | 2/1965 | Reichenberger |
| 3,187,963 A | 6/1965 | Anderson |
| 3,189,232 A | 6/1965 | Joffe |
| 3,191,867 A | 6/1965 | Helms |
| 3,240,389 A | 3/1966 | Genua |
| 3,334,627 A | 8/1967 | Gorman |
| 3,334,731 A | 8/1967 | Dale |
| 3,344,951 A | 10/1967 | Gervais |
| 3,361,306 A | 1/1968 | Grim |
| 3,402,863 A | 9/1968 | Green |
| 3,419,187 A | 12/1968 | Bazarnic |
| 3,446,179 A | 5/1969 | Bender |
| 3,477,561 A | 11/1969 | Espinal |
| 3,495,567 A | 2/1970 | Hayes et al. |
| 3,511,409 A | 5/1970 | Huck |
| 3,549,057 A | 12/1970 | Perez |
| 3,568,629 A | 3/1971 | Porter |
| 3,572,282 A | 3/1971 | Trump et al. |
| 3,589,563 A | 6/1971 | Carragan et al. |
| 3,612,349 A | 10/1971 | Thomas |
| 3,654,890 A | 4/1972 | Rigney et al. |
| 3,655,952 A | 4/1972 | Johnson et al. |
| 3,688,945 A | 9/1972 | Harman, Jr. et al. |
| 3,753,417 A | 8/1973 | Garby |
| 3,766,882 A | 10/1973 | Babbitt, III |
| 3,789,843 A | 2/1974 | Armstrong et al. |
| 3,792,242 A | 2/1974 | Hanson |
| 3,796,348 A | 3/1974 | Zipper |
| 3,797,748 A | 3/1974 | Nozawa et al. |
| 3,802,608 A | 4/1974 | Gullett |
| 3,831,808 A | 8/1974 | Bender |
| 3,831,812 A | 8/1974 | Dolan |
| 3,845,883 A | 11/1974 | Johnson et al. |
| 3,848,774 A | 11/1974 | Schimke |
| 3,886,879 A | 6/1975 | Frost et al. |
| 3,887,099 A | 6/1975 | Gillman et al. |
| 3,921,568 A | 11/1975 | Fish |
| 3,926,326 A | 12/1975 | Grau |
| 3,950,939 A | 4/1976 | Meisner |
| 3,960,713 A | 6/1976 | Carey |
| 3,977,554 A | 8/1976 | Costa |
| 3,994,421 A | 11/1976 | Hansen |
| 4,011,829 A | 3/1977 | Wachsmann et al. |
| 4,029,033 A | 6/1977 | Kerwin et al. |
| 4,034,757 A | 7/1977 | Glover |
| 4,037,719 A | 7/1977 | Perlmutter |
| 4,069,935 A | 1/1978 | Hampel |
| 4,069,942 A | 1/1978 | Marshall et al. |
| 4,078,661 A | 3/1978 | Thomas |
| 4,094,408 A | 6/1978 | Ford |
| 4,114,811 A | 9/1978 | Loeffler |
| 4,162,746 A | 7/1979 | Anderson et al. |
| 4,164,301 A | 8/1979 | Thayer |
| 4,188,984 A | 2/1980 | Lyall |
| 4,220,247 A | 9/1980 | Kramer |
| 4,291,688 A | 9/1981 | Kistler |
| 4,300,548 A | 11/1981 | Jones |
| 4,319,128 A | 3/1982 | Dow, Jr. et al. |
| 4,339,056 A | 7/1982 | Berkstresser, Jr. et al. |
| 4,345,541 A | 8/1982 | Villa-Real |
| 4,347,804 A | 9/1982 | Villa-Real |
| 4,347,853 A | 9/1982 | Gereg et al. |
| 4,350,265 A | 9/1982 | Griffiths et al. |
| 4,354,621 A | 10/1982 | Knickerbocker |
| 4,357,192 A | 11/1982 | Moser |
| 4,365,722 A | 12/1982 | Kramer |
| 4,368,381 A | 1/1983 | Ishiyama |
| 4,405,045 A | 9/1983 | Villa-Real |
| 4,419,016 A | 12/1983 | Zoltan |
| 4,432,300 A | 2/1984 | Lyss |
| 4,436,223 A | 3/1984 | Wilson |
| 4,440,306 A | 4/1984 | Van Buskirk et al. |
| 4,489,834 A | 12/1984 | Thackrey |
| 4,500,005 A | 2/1985 | Forrester |
| 4,501,370 A | 2/1985 | Kelley |
| 4,509,515 A | 4/1985 | Altounyan et al. |
| 4,511,150 A | 4/1985 | Seguenot |
| 4,523,933 A | 6/1985 | Laush et al. |
| 4,528,933 A | 7/1985 | Allen |
| 4,534,345 A | 8/1985 | Wetterlin |
| 4,538,744 A | 9/1985 | Weissenborn |
| 4,548,157 A | 10/1985 | Hevoyan |
| 4,562,933 A | 1/1986 | Dennis |
| 4,565,302 A | 1/1986 | Pfeiffer et al. |
| 4,599,508 A | 7/1986 | Smetaniuk |
| 4,634,012 A | 1/1987 | Kelley |
| 4,637,528 A | 1/1987 | Wachinski et al. |
| 4,641,759 A | 2/1987 | Kelley |
| 4,646,936 A | 3/1987 | Frazier et al. |
| 4,662,520 A | 5/1987 | Griffin |
| 4,664,107 A | 5/1987 | Wass |
| 4,666,051 A | 5/1987 | Trick |
| 4,668,218 A | 5/1987 | Virtanen |
| 4,677,975 A | 7/1987 | Edgar et al. |
| 4,693,399 A | 9/1987 | Hickman et al. |
| 4,705,182 A | 11/1987 | Newel-Lewis |
| 4,722,729 A | 2/1988 | Dettbarn et al. |
| 4,723,673 A | 2/1988 | Tartaglia et al. |
| 4,727,886 A | 3/1988 | Conrardy et al. |
| 4,736,871 A | 4/1988 | Luciani et al. |
| 4,749,093 A | 6/1988 | Trick |
| 4,753,189 A | 6/1988 | Mastman et al. |
| 4,756,423 A | 7/1988 | Holtsch |
| 4,782,966 A | 11/1988 | Thackrey |
| 4,792,664 A | 12/1988 | Schwab |
| 4,817,822 A | 4/1989 | Rand et al. |
| 4,890,572 A | 1/1990 | Huang |
| 4,934,358 A | 6/1990 | Nilsson et al. |
| 4,947,875 A | 8/1990 | Brooks et al. |
| 4,955,371 A | 9/1990 | Zamba et al. |
| 4,969,578 A | 11/1990 | Gander et al. |
| 4,973,250 A | 11/1990 | Milman |
| 4,984,158 A | 1/1991 | Hillsman |
| 5,009,338 A | 4/1991 | Barker |
| 5,011,032 A | 4/1991 | Rollman |
| 5,020,527 A | 6/1991 | Dessertine |
| 5,027,806 A | 7/1991 | Zoltan et al. |
| 5,027,808 A | 7/1991 | Rich et al. |
| 5,038,972 A | 8/1991 | Muderlak et al. |
| 5,060,643 A | 10/1991 | Rich et al. |
| 5,069,204 A | 12/1991 | Smith et al. |
| 5,082,129 A | 1/1992 | Kramer |
| 5,082,130 A | 1/1992 | Weinstein |
| 5,115,929 A | 5/1992 | Buono |
| 5,174,473 A | 12/1992 | Marelli |
| 5,184,761 A | 2/1993 | Lee |
| 5,188,251 A | 2/1993 | Kusz |
| 5,190,643 A | 3/1993 | Duncan et al. |
| 5,209,375 A | 5/1993 | Fuchs |
| 5,215,079 A | 6/1993 | Fine et al. |
| 5,217,004 A | 6/1993 | Blasnik et al. |
| 5,224,474 A | 7/1993 | Bloomfield |

(56) References Cited

U.S. PATENT DOCUMENTS

| | | | |
|---|---|---|---|
| 5,227,764 A | 7/1993 | Umemoto |
| 5,228,586 A | 7/1993 | Fuchs |
| 5,242,067 A | 9/1993 | Garby et al. |
| 5,243,970 A | 9/1993 | Amrosio et al. |
| 5,261,548 A | 11/1993 | Barker et al. |
| 5,263,475 A | 11/1993 | Altermatt et al. |
| 5,284,133 A | 2/1994 | Burns et al. |
| 5,289,946 A | 3/1994 | Fuchs |
| 5,299,701 A | 4/1994 | Barker et al. |
| 5,300,042 A | 4/1994 | Kossoff et al. |
| 5,301,873 A | 4/1994 | Burke et al. |
| 5,328,597 A | 7/1994 | Boldt, Jr. et al. |
| 5,331,953 A | 7/1994 | Andersson et al. |
| 5,335,823 A | 8/1994 | Fuchs et al. |
| 5,349,944 A | 9/1994 | Chippendale et al. |
| 5,349,945 A | 9/1994 | Wass et al. |
| 5,356,012 A | 10/1994 | Tang et al. |
| 5,363,842 A | 11/1994 | Mishelevich et al. |
| 5,370,267 A | 12/1994 | Schroeder |
| 5,382,243 A | 1/1995 | Mulholland |
| RE34,847 E | 2/1995 | Muderlak et al. |
| 5,388,572 A | 2/1995 | Mulhauser et al. |
| 5,392,768 A | 2/1995 | Johansson et al. |
| 5,394,866 A | 3/1995 | Ritson et al. |
| 5,397,028 A | 3/1995 | Jesadanont |
| 5,411,173 A | 5/1995 | Weinstein |
| 5,421,482 A | 6/1995 | Garby et al. |
| 5,437,270 A | 8/1995 | Braithwaite |
| 5,447,150 A | 9/1995 | Bacon |
| 5,448,042 A | 9/1995 | Robinson et al. |
| 5,482,030 A | 1/1996 | Klein |
| 5,482,163 A | 1/1996 | Hoffman |
| 5,505,192 A | 4/1996 | Samiotes et al. |
| 5,505,195 A | 4/1996 | Wolf et al. |
| 5,509,905 A | 4/1996 | Michel |
| 5,519,197 A | 5/1996 | Robinson et al. |
| 5,520,166 A | 5/1996 | Ritson et al. |
| 5,522,378 A | 6/1996 | Ritson et al. |
| 5,544,647 A | 8/1996 | Jewett et al. |
| 5,549,101 A | 8/1996 | Trofast et al. |
| 5,564,414 A | 10/1996 | Walker et al. |
| 5,574,268 A | 11/1996 | Herman et al. |
| 5,611,444 A | 3/1997 | Garby et al. |
| 5,617,844 A | 4/1997 | King |
| 5,622,163 A | 4/1997 | Jewett et al. |
| 5,625,334 A | 4/1997 | Compton |
| 5,625,659 A | 4/1997 | Sears |
| 5,638,970 A | 6/1997 | Garby et al. |
| 5,647,508 A * | 7/1997 | Ronci et al. ............... 222/23 |
| 5,657,748 A | 8/1997 | Braithwaite |
| 5,664,557 A | 9/1997 | Makiej, Jr. |
| 5,676,129 A | 10/1997 | Rocci, Jr. et al. |
| 5,687,710 A | 11/1997 | Ambrosio et al. |
| 5,692,492 A | 12/1997 | Bruna et al. |
| 5,694,882 A | 12/1997 | Marshall |
| 5,718,355 A | 2/1998 | Garby et al. |
| 5,724,957 A | 3/1998 | Rubsamen et al. |
| 5,732,836 A | 3/1998 | Barker et al. |
| 5,740,792 A | 4/1998 | Ashley et al. |
| 5,758,638 A | 6/1998 | Kreamer |
| 5,772,074 A | 6/1998 | Dial et al. |
| 5,794,612 A | 8/1998 | Wachter et al. |
| 5,799,651 A | 9/1998 | Garby et al. |
| 5,803,283 A | 9/1998 | Barker et al. |
| 5,809,997 A | 9/1998 | Wolf |
| 5,826,571 A | 10/1998 | Casper et al. |
| 5,829,434 A | 11/1998 | Ambrosio et al. |
| 5,845,777 A | 12/1998 | Najmi |
| 5,852,590 A | 12/1998 | de la Huerga |
| 5,855,307 A * | 1/1999 | Biddick et al. ............... 224/267 |
| 5,871,007 A | 2/1999 | Clark, Jr. |
| 5,873,995 A | 2/1999 | Huang et al. |
| 5,882,507 A | 3/1999 | Tanner et al. |
| 5,896,855 A | 4/1999 | Hobbs |
| 5,896,990 A | 4/1999 | Barzana |
| 5,899,201 A | 5/1999 | Schultz et al. |
| 5,904,139 A | 5/1999 | Hauser |
| 5,957,896 A | 9/1999 | Bendek et al. |
| 5,988,496 A | 11/1999 | Bruna |
| 6,000,159 A | 12/1999 | Hornung |
| 6,012,450 A | 1/2000 | Rubsamen |
| 6,029,659 A | 2/2000 | O'Connor |
| 6,059,133 A | 5/2000 | Lai |
| 6,062,214 A | 5/2000 | Howlett |
| 6,076,521 A | 6/2000 | Lindahl et al. |
| 6,082,358 A | 7/2000 | Scarrott et al. |
| 6,089,180 A | 7/2000 | Nichols, Jr. |
| 6,119,684 A | 9/2000 | Nohl et al. |
| 6,138,669 A | 10/2000 | Rocci, Jr. et al. |
| 6,142,339 A | 11/2000 | Blacker et al. |
| 6,148,815 A | 11/2000 | Wolf |
| 6,149,054 A | 11/2000 | Cirrillo |
| 6,155,251 A | 12/2000 | Hauser |
| 6,161,724 A | 12/2000 | Blacker et al. |
| 6,164,494 A | 12/2000 | Marelli |
| 6,193,114 B1 * | 2/2001 | Hopkins ............... 222/330 |
| 6,202,642 B1 | 3/2001 | McKinnon et al. |
| 6,223,744 B1 | 5/2001 | Garon |
| 6,234,168 B1 | 5/2001 | Bruna |
| 6,283,365 B1 | 9/2001 | Bason |
| 6,305,371 B1 | 10/2001 | Frid et al. |
| 6,328,037 B1 | 12/2001 | Scarrott et al. |
| 6,336,453 B1 | 1/2002 | Scarrott et al. |
| 6,360,739 B1 | 3/2002 | Rand et al. |
| 6,405,727 B1 | 6/2002 | MacMichael et al. |
| 6,415,785 B1 | 7/2002 | Stage |
| 6,425,392 B1 | 7/2002 | Sosiak |
| 6,431,168 B1 | 8/2002 | Rand et al. |
| 6,435,372 B1 | 8/2002 | Blacker et al. |
| 6,446,627 B1 | 9/2002 | Bowman et al. |
| 6,450,724 B1 | 9/2002 | Cambio |
| 6,474,331 B1 | 11/2002 | Rand et al. |
| 6,481,438 B1 | 11/2002 | Gallem et al. |
| 6,484,717 B1 | 11/2002 | Dagsland et al. |
| 6,516,799 B1 | 2/2003 | Greenwood et al. |
| 6,529,446 B1 | 3/2003 | de la Huerga |
| 6,561,384 B2 | 5/2003 | Blacker et al. |
| 6,601,582 B2 | 8/2003 | Rand et al. |
| 6,615,827 B2 | 9/2003 | Greenwood et al. |
| 6,659,307 B1 | 12/2003 | Stradella |
| 6,679,251 B1 * | 1/2004 | Gallem et al. ............ 128/200.23 |
| 6,701,917 B2 | 3/2004 | O'Leary |
| 6,718,972 B2 | 4/2004 | O'Leary |
| 6,729,330 B2 | 5/2004 | Scarrott et al. |
| 6,752,153 B1 | 6/2004 | Eckert |
| 6,761,161 B2 | 7/2004 | Scarrott et al. |
| 6,766,799 B2 | 7/2004 | Edwards et al. |
| 6,805,116 B2 | 10/2004 | Hodson |
| 6,907,876 B1 | 6/2005 | Clark et al. |
| 6,981,618 B2 * | 1/2006 | Reisinger ............ 222/326 |
| 6,997,349 B2 | 2/2006 | Blacker et al. |
| 7,004,164 B2 | 2/2006 | Scarrott |
| 7,331,340 B2 | 2/2008 | Barney |
| 7,464,708 B2 | 12/2008 | Marx |
| 7,819,116 B2 | 10/2010 | Brand et al. |
| 2002/0153005 A1 | 10/2002 | Scarrott et al. |
| 2003/0183225 A1 | 10/2003 | Knudsen |
| 2003/0183226 A1 | 10/2003 | Brand et al. |
| 2003/0200964 A1 | 10/2003 | Blakley et al. |
| 2003/0205227 A1 | 11/2003 | Hodson |
| 2003/0209239 A1 | 11/2003 | Rand et al. |
| 2004/0065326 A1 | 4/2004 | MacMichael |
| 2004/0069301 A1 | 4/2004 | Bacon |
| 2004/0089292 A1 | 5/2004 | Pollet et al. |
| 2004/0144798 A1 | 7/2004 | Ouyang et al. |
| 2004/0149772 A1 | 8/2004 | Ouyang |
| 2004/0149773 A1 | 8/2004 | Ouyang et al. |
| 2004/0221840 A1 | 11/2004 | Stockman-Lamb |
| 2004/0255935 A1 | 12/2004 | Bruna |
| 2004/0255936 A1 | 12/2004 | Urbanus |
| 2005/0011515 A1 | 1/2005 | Lee et al. |
| 2006/0180606 A1 | 8/2006 | Lu et al. |
| 2007/0084462 A1 | 4/2007 | Allen |

(56) References Cited

U.S. PATENT DOCUMENTS

| | | | |
|---|---|---|---|
| 2007/0241136 A1 | 10/2007 | Poulard et al. | |
| 2008/0017188 A1 | 1/2008 | Pardonge et al. | |
| 2010/0101566 A1 | 4/2010 | Fenlon | |

FOREIGN PATENT DOCUMENTS

| | | | |
|---|---|---|---|
| CA | 2 152 088 A | 7/1994 |
| CA | 2 181 789 C | 6/1996 |
| CA | 2 486 892 A1 | 12/1998 |
| CA | 2 315 777 A1 | 7/1999 |
| CA | 2 331 179 A1 | 11/1999 |
| CA | 2 383 425 A1 | 3/2001 |
| CA | 2 388 958 A1 | 3/2001 |
| CA | 2 414 118 A1 | 1/2002 |
| CA | 2 420 171 A1 | 3/2002 |
| DE | 6 603 758 | 7/1969 |
| DE | 27 02 539 A1 | 1/1977 |
| DE | 33 36 486 A1 | 4/1984 |
| DE | 85 90 143.1 | 10/1985 |
| DE | 86 02 238.5 | 5/1986 |
| EP | 0 028 929 A2 | 5/1981 |
| EP | 0 098 939 A2 | 1/1984 |
| EP | 0 114 617 A2 | 8/1984 |
| EP | 0 063 599 | 6/1986 |
| EP | 0 230 323 B1 | 7/1987 |
| EP | 0 236 871 A2 | 9/1987 |
| EP | 0 269 496 A2 | 6/1988 |
| EP | 0 280 104 B1 | 8/1988 |
| EP | 0 488 609 A1 | 6/1992 |
| EP | 0 559 757 B1 | 9/1993 |
| EP | 0 839 544 A2 | 5/1998 |
| EP | 0 949 584 A2 | 10/1999 |
| EP | 1 163 922 A2 | 12/2001 |
| EP | 1 369 139 A1 | 12/2003 |
| EP | 1 220 802 B1 | 2/2004 |
| EP | 966309 B2 | 6/2004 |
| EP | 1475116 A2 | 11/2004 |
| FR | 1 113 454 A | 3/1956 |
| FR | 2 743 055 | 7/1997 |
| FR | 0451164 | 6/2004 |
| GB | 11635 A | 0/1911 |
| GB | 998 148 | 7/1965 |
| GB | 1 058 636 | 2/1967 |
| GB | 1 290 484 | 9/1972 |
| GB | 1 317 315 | 5/1973 |
| GB | 2 036 695 A | 7/1980 |
| GB | 2 063 075 A | 6/1981 |
| GB | 2 092 991 A | 8/1982 |
| GB | 2 104 393 A | 3/1983 |
| GB | 2 191 032 A | 12/1987 |
| GB | 2 195 544 A | 4/1988 |
| GB | 2 348 928 A | 10/2000 |
| GB | 2 414 187 A | 11/2005 |
| JP | 61-55759 | 4/1986 |
| JP | 04-50059 | 4/1992 |
| JP | 6-26891 | 4/1994 |
| WO | WO 86/02275 | 4/1986 |
| WO | WO 87/04354 | 8/1987 |
| WO | WO 90/10470 | 9/1990 |
| WO | WO 91/06334 | 5/1991 |
| WO | WO 92/07600 | 5/1992 |
| WO | WO 92/09324 | 6/1992 |
| WO | WO 92/15353 | 9/1992 |
| WO | WO 92/17231 | 10/1992 |
| WO | WO 92/17231 A1 | 10/1992 |
| WO | WO 93/24167 | 12/1993 |
| WO | WO 94/11272 | 5/1994 |
| WO | WO 94/14492 | 7/1994 |
| WO | WO 95/34874 | 12/1995 |
| WO | WO 96/16686 | 6/1996 |
| WO | WO 96/16687 | 6/1996 |
| WO | WO 96/39337 | 12/1996 |
| WO | WO 98/01822 | 1/1998 |
| WO | WO 98/28033 A2 | 7/1998 |
| WO | WO 98/56444 | 12/1998 |
| WO | WO 98/56445 | 12/1998 |
| WO | WO 99/36115 | 7/1999 |
| WO | WO 99/57019 | 11/1999 |
| WO | WO 00/09187 | 2/2000 |
| WO | WO 00/16836 A1 | 3/2000 |
| WO | WO 00/59806 | 10/2000 |
| WO | WO 01/08733 A1 | 2/2001 |
| WO | WO 01/28887 A1 | 4/2001 |
| WO | WO 01/29765 A1 | 4/2001 |
| WO | WO 01/37909 A1 | 5/2001 |
| WO | WO 02/053295 A1 | 7/2002 |
| WO | WO 02/092152 A1 | 11/2002 |
| WO | WO 03/101514 A1 | 12/2003 |
| WO | WO 03/103759 A1 | 12/2003 |
| WO | WO 2004/089451 A1 | 10/2004 |
| WO | WO 2006/064159 A1 | 6/2006 |
| WO | WO 2008/104366 A1 | 9/2008 |

OTHER PUBLICATIONS

Written Opinion of the International Searching Authority in International Application No. PCT/IB2006/000084, dated Jun. 2, 2006, 8 pages.
English language translation of Office Action in Japanese Application No. 2008-019458 dispatched Sep. 29, 2009, 2 pages.
International Search Report for International Application No. PCT/FR2005/051078, dated Apr. 21, 2006, 4 pages.
International Search Report for International Application No. PCT/EP2008/001514, dated Jun. 9, 2008, 2 pages.
Translation of International Preliminary Report on Patentability for International Application No. PCT/FR2005/051078, dated Oct. 15, 2007, 6 pages.
International Preliminary Report on Patentability for International Application No. PCT/EP2008/001514, dated Sep. 1, 2009, 7 pages.

* cited by examiner

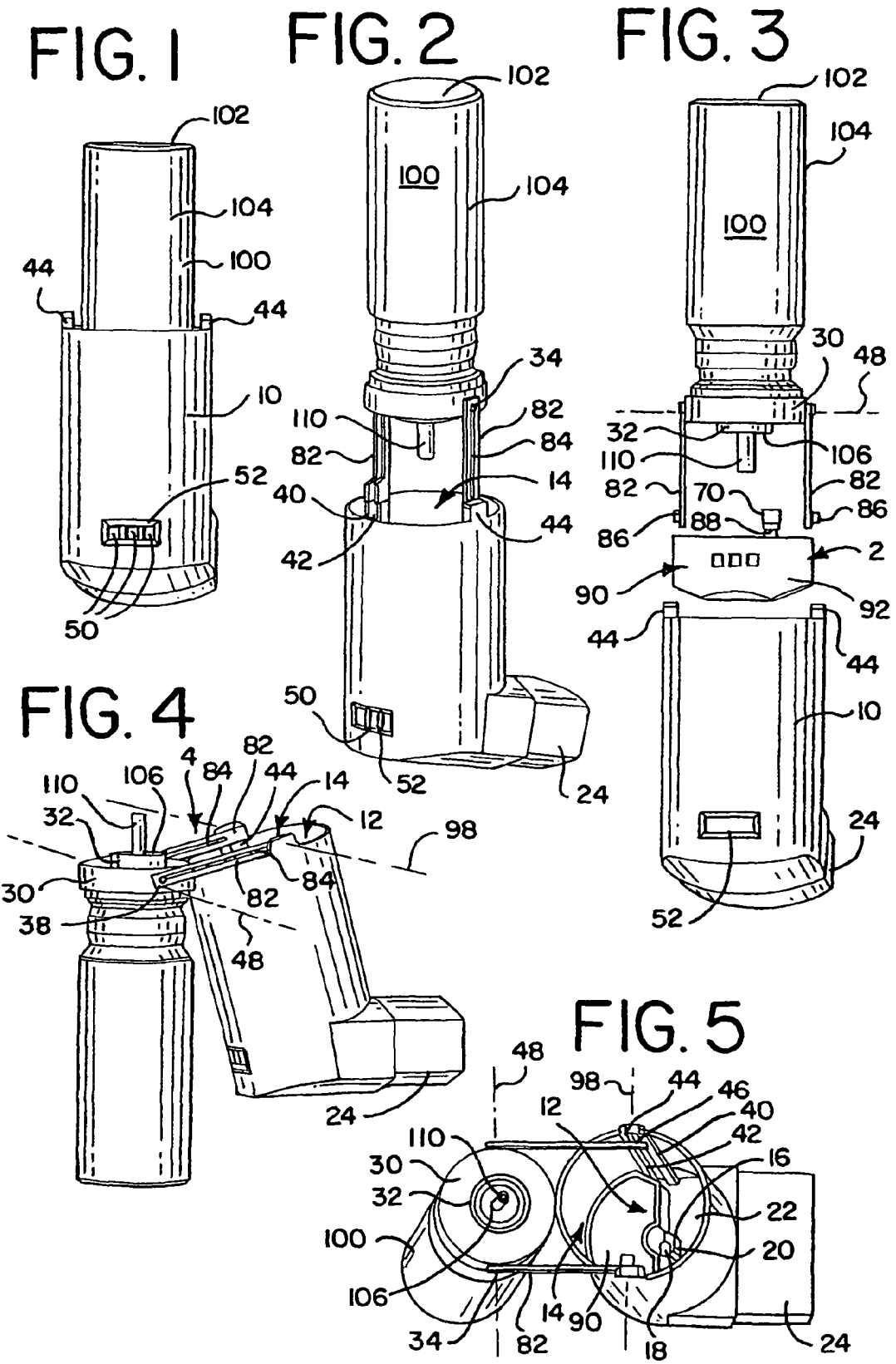

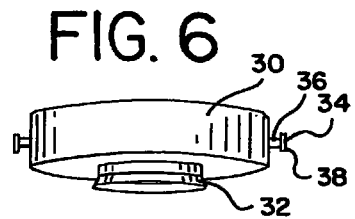
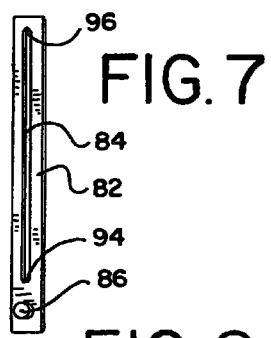
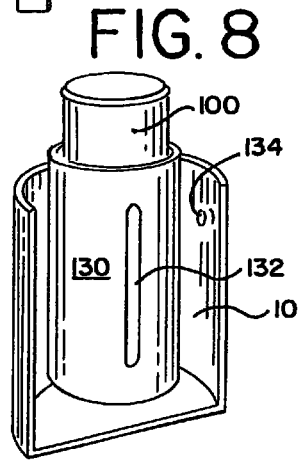
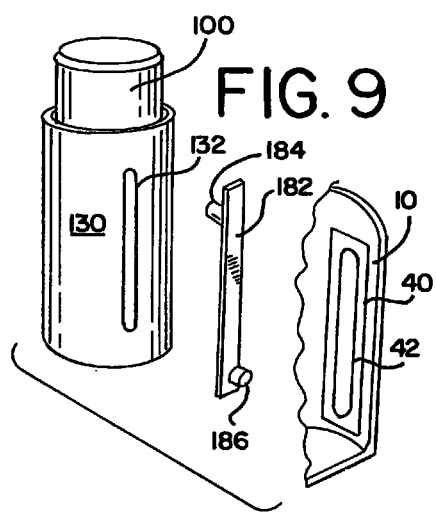
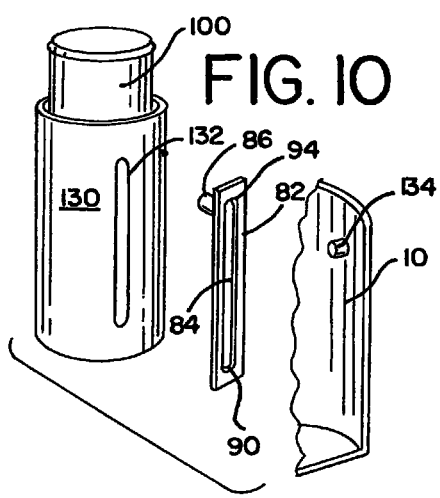
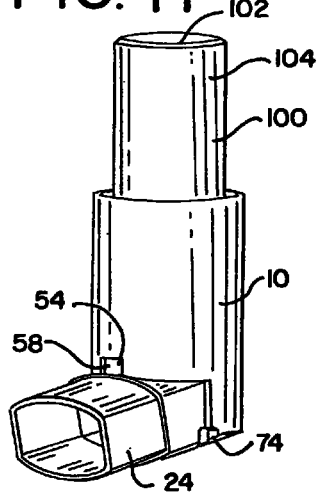

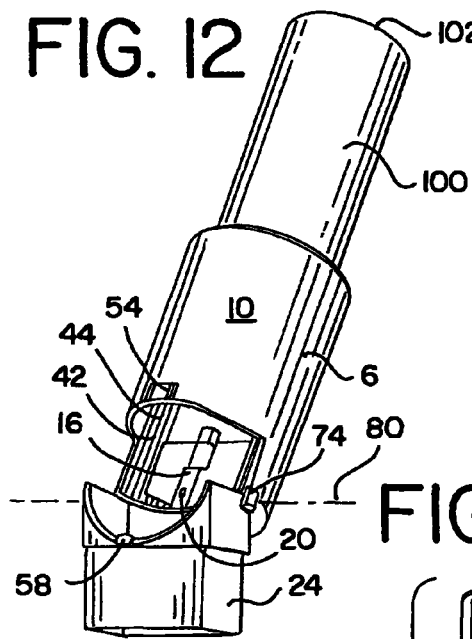
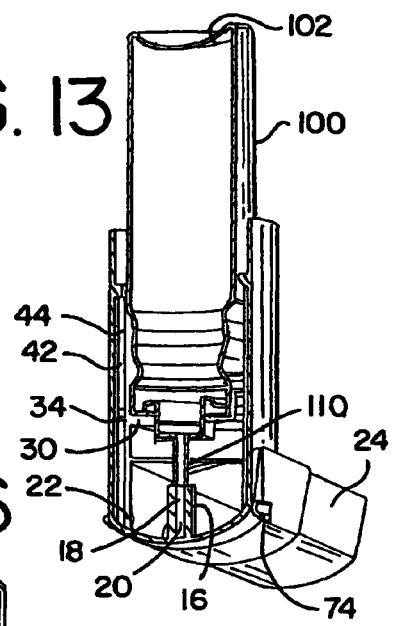
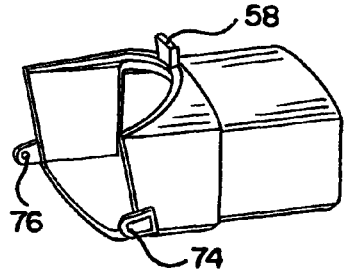
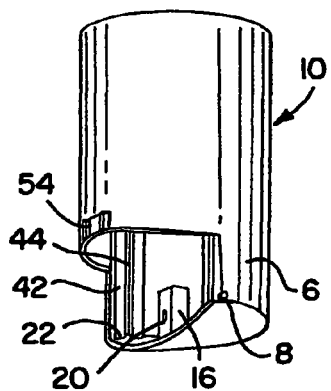
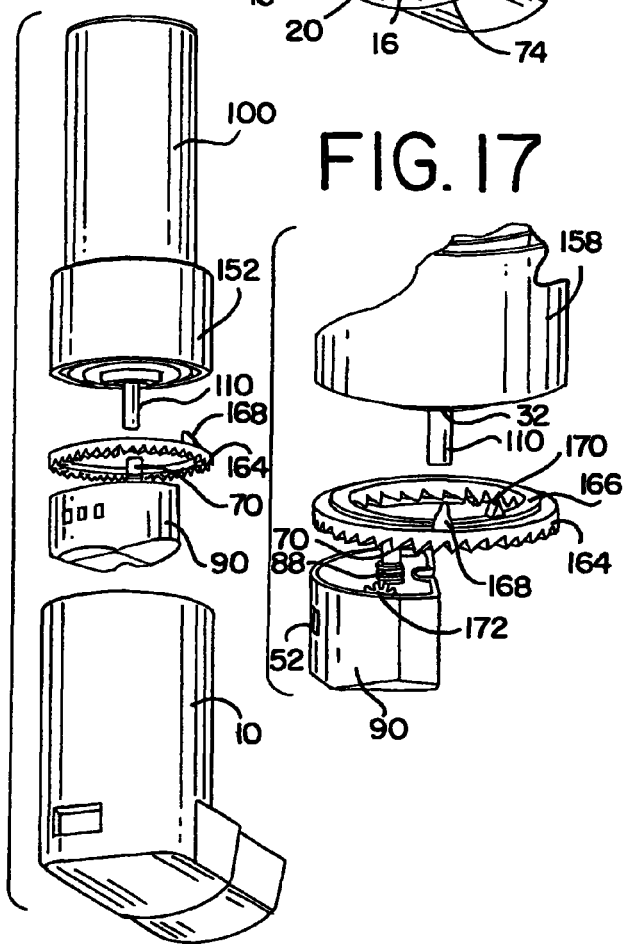

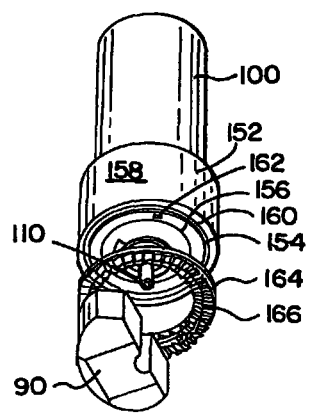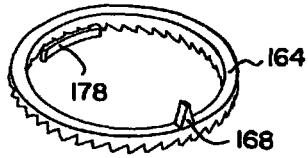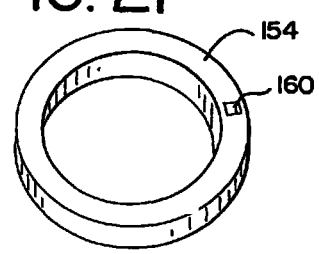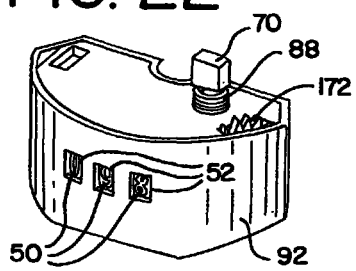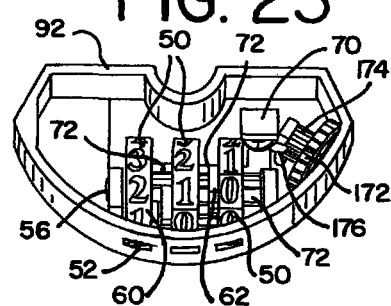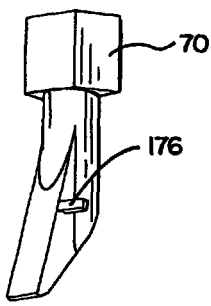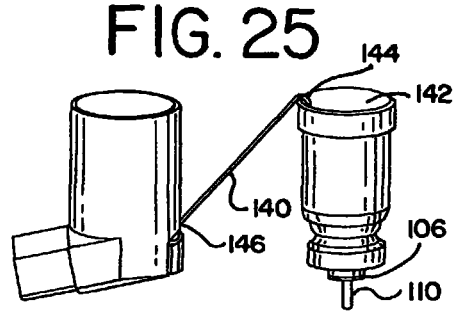

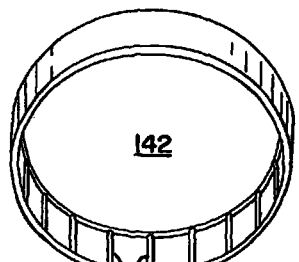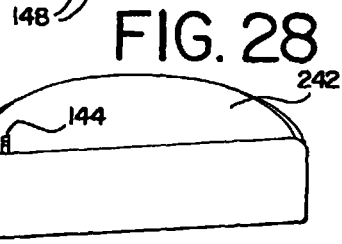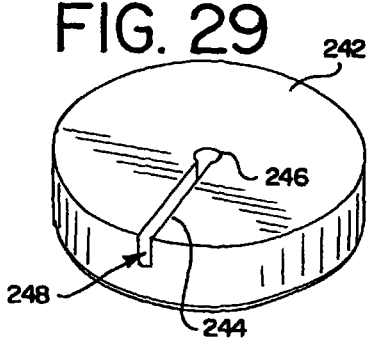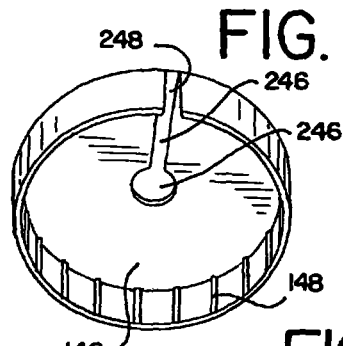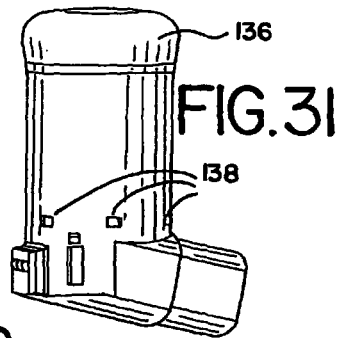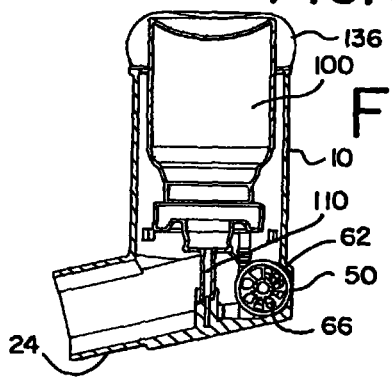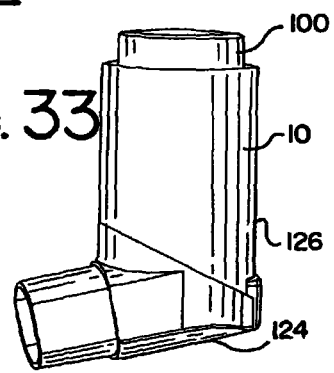

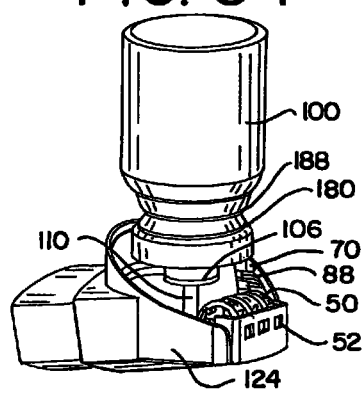
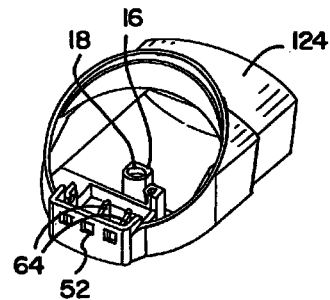
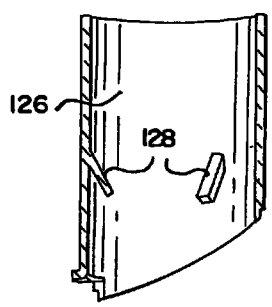
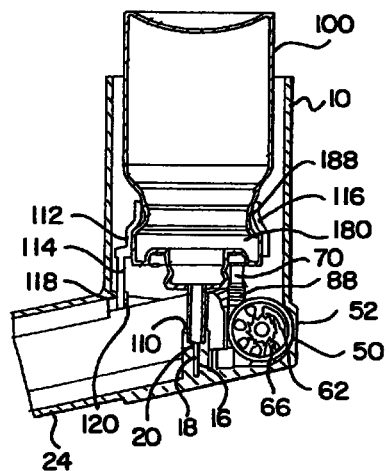
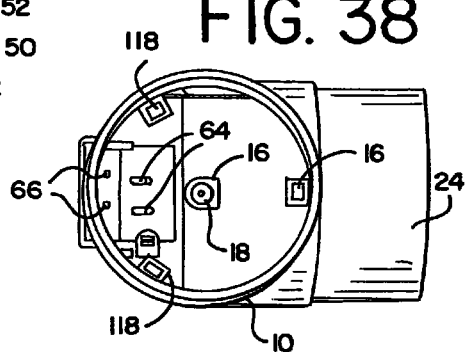
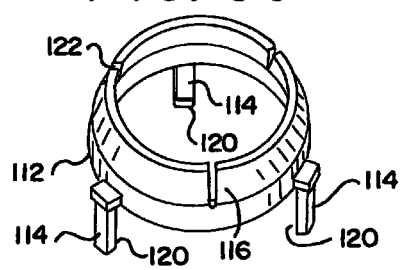

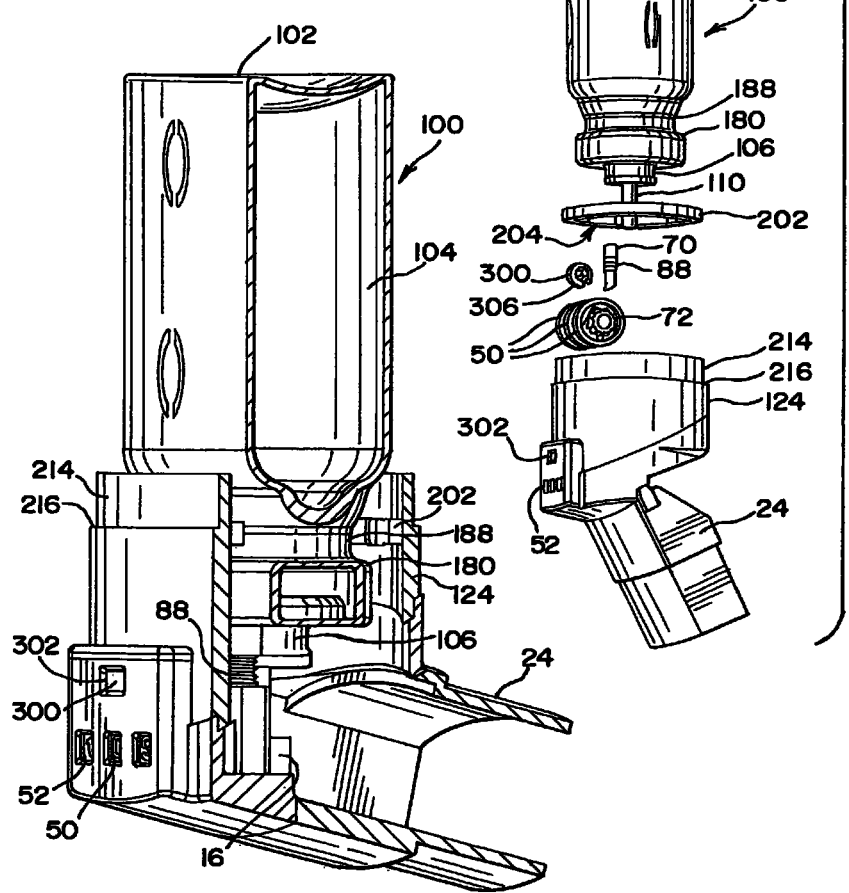

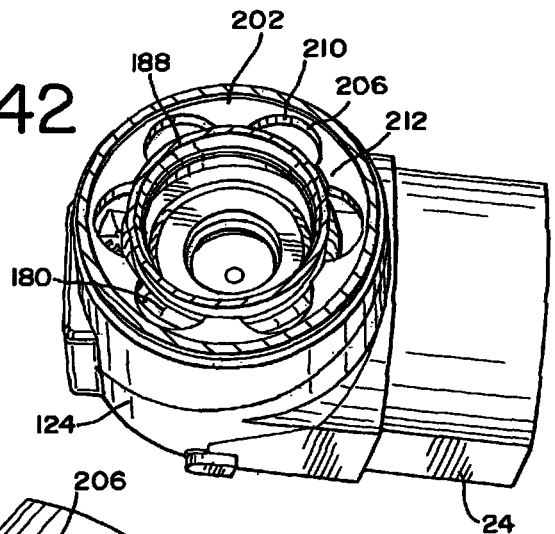
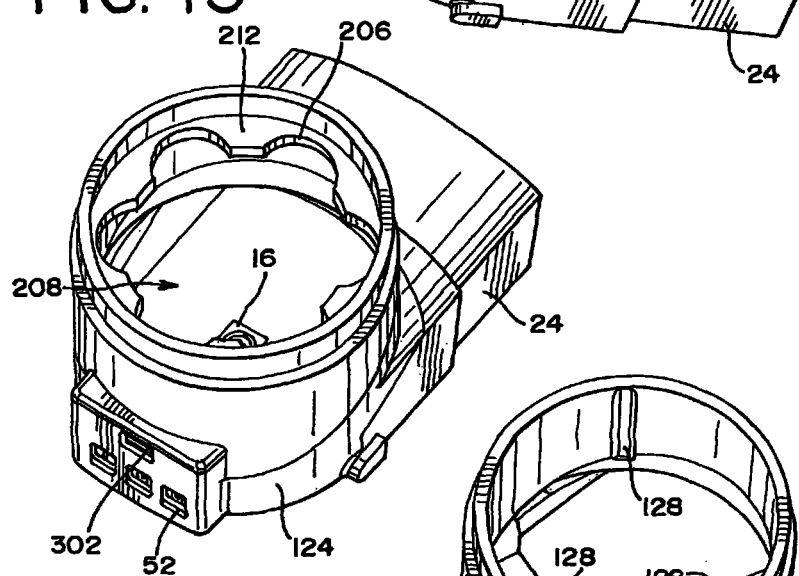
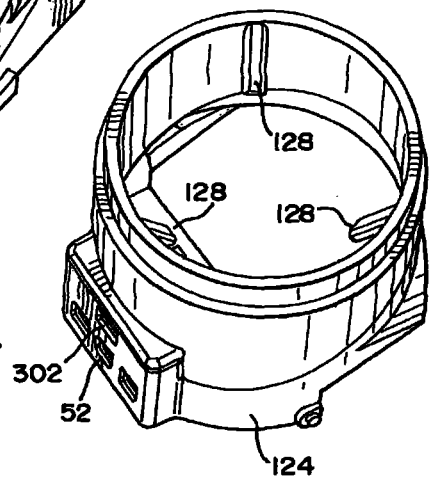

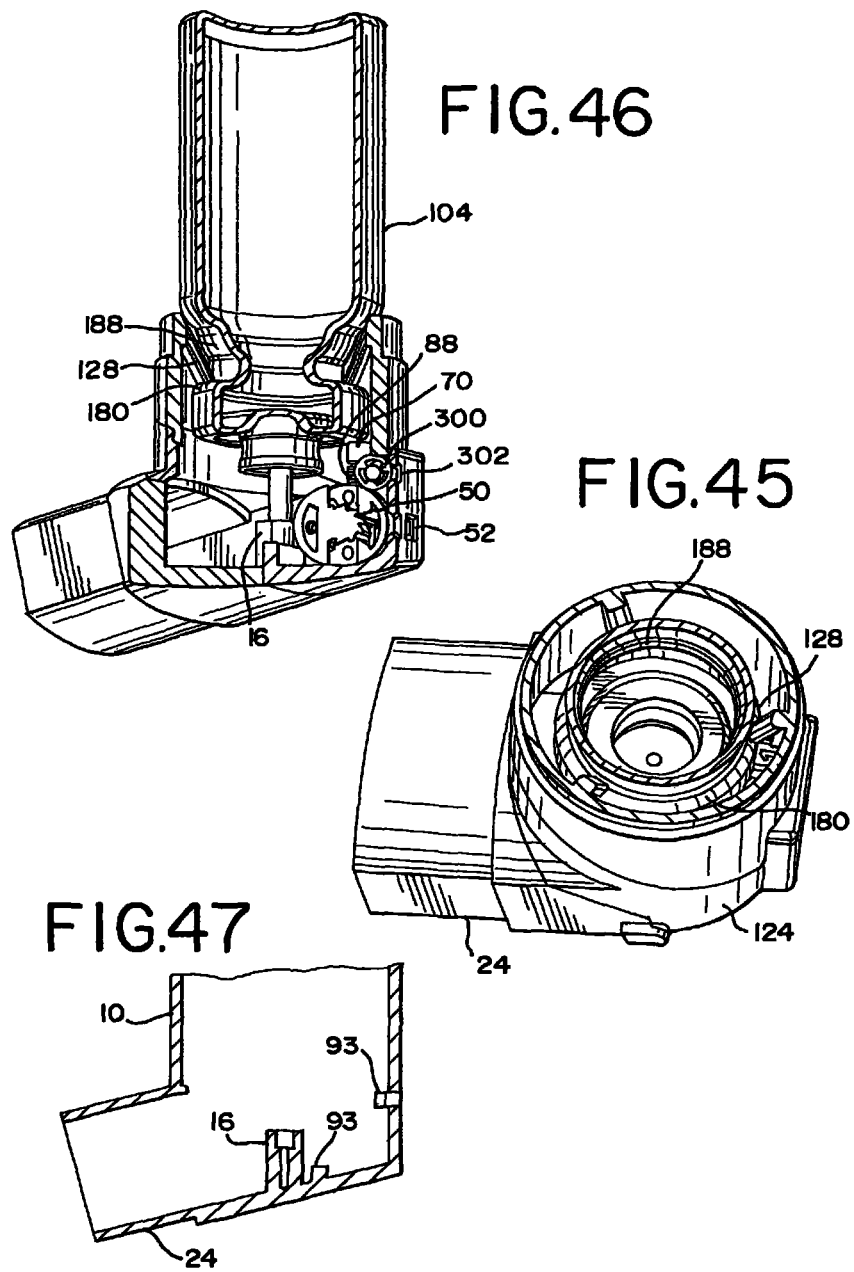

DISPENSING DEVICE

This application is a continuation of U.S. application Ser. No. 11/334,940, filed Jan. 19, 2006 now U.S. Pat. No. 7,886,934, which claims the benefit of U.S. Provisional Patent Application Ser. No. 60/671,220, filed Apr. 14, 2005 and entitled "Dispensing Device," and U.S. Provisional Patent Application Ser. No. 60/645,095, filed Jan. 20, 2005 and entitled "Dispensing Device," the entire disclosures of which are hereby incorporated herein by reference.

FIELD OF THE INVENTION

The present invention relates generally to a dispensing device, and in particular, to a dispensing device having a dosage indicator for indicating the number of metered dosages that have been dispensed from, or remain in, a container that is associated with that particular dispensing device.

BACKGROUND

Aerosol dispensing devices have been developed that include a dose indicating device to indicate the number of metered doses that have been dispensed from the device, or to indicate the number of doses remaining therein. For example, patients have certain conditions that can be treated with medicaments dispensed in an aerosol and administered to the patient by inhalation. In one format, the aerosol with medicaments are contained in a container, and dispensed in metered, or measured, dosages with an inhalation device, or actuator boot. In such an arrangement, it can be important for the patient to be able to ascertain the number of metered doses remaining in the container, either by an indication of the number remaining therein or by knowledge of the number already dispensed therefrom, such that the patient is not caught unaware with an empty container when in need of the medicament. Thus, it may be important for the inhalation device to provide an accurate indication of either the number of doses remaining in the container, or the number of doses already dispensed therefrom.

In addition, a particular actuator boot may be particularly suited or specially configured for dispensing a particular medicament from the container. Therefore, it may also be important for the container and/or actuator boot to be configured to work with only a corresponding or associated actuator boot and/or container.

Typically, a conventional aerosol container includes a body and a valve stem that can be depressed relative to the body so as to emit the metered dose of aerosol and medicament. The container typically is supplied with a predetermined number of metered doses, generally on the order of about 200, such that the counting of the number of valve stem depressions, and corresponding number of dispensed metered doses, can be directly correlated with the number of doses remaining in the container.

In operation, the container is typically received within a housing of the inhalation device, wherein the valve is brought into engagement with a support block in the housing. The user administers the medicament by moving the container relative to the housing so as to depress the valve stem and internal valve and thereby release a metered dose, which is typically administered to the user through a port or mouthpiece extending from the housing. After the dose is administered, the valve stem, which is typically spring loaded, biases the container away from the support block so as to again move the container relative to the housing. In this way, a metered dose of medicament is administered by each cycle of linear reciprocal movement of the container relative to the housing.

Some actuator boots, or other devices attached to the medicament container, have indicating devices that convert the linear reciprocal movement of the container relative to the housing into a one-way, or single-cycle, movement of an indicator, wherein the indicator identifies the relative fullness of the container, the number of metered doses remaining therein or the number of doses already administered. Often, the indicator is disposed inside the actuator boot. If the container is removed from the actuator boot, for example to clean the actuator boot, a different container may inadvertently be inserted into the actuator boot, thereby corrupting the count or adversely affecting the ability of the actuator boot to properly dispense the substance.

To solve this problem, some devices, including the indicator, are secured to the container, as shown for example in U.S. Pat. No. 6,431,168 to Rand. In the '168 patent to Rand, however, the indicators move with the container as it moves relative to the actuator boot. Therefore, the indicator member moves relative to the viewing window in the actuator boot, which can be a distraction and can create confusion and difficulties in reading the device, thereby calling into question the accuracy and robustness of the device.

SUMMARY

Briefly stated, in one aspect the invention is directed to a dispenser that dispenses dosages of a substance. The dispenser includes a container having an end portion and a valve stem extending from the end portion. A dispenser housing includes a top, a bottom and a longitudinally extending cavity defining an opening in the top. The bottom defines a well. An indicating device is connected to the dispenser housing and includes an indicator with dosage indicia. A connector connects the dispenser housing and the container. The container is moveable between an engaged position, wherein the valve stem is disposed in the well and a disengaged position, wherein the valve stem is removed from the well. The connector maintains a connection between the container and the dispenser housing as the container is moved between the engaged and the disengaged positions.

In one embodiment, the connector includes a track and follower formed on one of a mounting portion mounted to the container and the dispenser housing. In one embodiment, the connector further includes an extension member connecting the mounting portion and the dispenser. The extension member can also include a track and/or one or more followers.

In an alternative embodiment, the connector includes a tether connecting the container and the dispenser housing. In one embodiment, the tether is made of a stretchable material.

In another aspect, the dispenser includes the dispenser housing, the indicating device and a connector having a mounting portion adapted to be connected to the container. The connector is connected to the dispenser housing with the mounting portion being moveable between a first position and a second position spaced from the first position.

In yet another aspect, a method for removing at least a portion of a container from a dispenser housing includes moving the container from an engaged position to a disengaged position and thereby removing the valve stem from the well. The connector maintains a connection between the container and the dispenser housing as the container is moved to the disengaged position.

In yet another aspect, a dispenser includes a dispenser housing, a key device and an indicating device. The key device has a mounting portion adapted to be connected to the container, and includes first and second rotatable rings. The indicating device is connected to the dispenser housing and includes an indicator having dosage indicia and first and second gears. One of the first ring and the first gear has a first key portion and the other of the first ring and the first gear has a first key passageway. Likewise, one of the second ring and the second gear has a second key portion and the other of the second ring and the second gear has a second key passageway. The key device is moveable between an engaged position wherein the first and second key portions are positioned in the first and second key passageways respectively and a disengaged position wherein the first and second key portions are removed from the first and second key passageways respectively.

In yet another aspect, the dispenser further includes the container, which has a canister and a valve stem. The valve stem is reciprocally moveable relative to the canister to release a dose of substance. The container is moveable between an engaged position wherein the first and second key portions are positioned in the first and second key passageways respectively and the valve stem is engaged with the dispenser housing, and a disengaged position wherein the first and second key portions are removed from said first and second key passageways respectively and the valve stem is removed from the well.

In yet another aspect, a method for operating a dispenser includes reciprocally moving the canister relative to the valve stem and dispensing a dosage of substance from the container upon each reciprocal movement of the canister. The method further includes rotating the first gear a first incremental amount in response to each reciprocal movement of the canister, selectively engaging the second gear with the first gear upon a predetermined number of reciprocal movements of the canister, and rotating the second gear a second incremental amount with the first gear. The method further includes moving the container from an engaged position, wherein the first and second key portions are positioned in the first and second key passageways respectively and the valve stem is engaged with the dispenser housing, to a disengaged position, wherein the first and second key portions are removed from the first and second key passageways respectively and the valve stem is removed from the well.

The various embodiments provide simple, robust and inexpensive solutions for providing the user with information allowing them to ascertain the number of metered doses remaining in the container, either by an indication of the number remaining therein or by knowledge of the number already dispensed therefrom. In addition, in some of the embodiments, the container remains connected to the dispenser housing, even if it is removed therefrom, thereby ensuring that the integrity of the dose count for the container is preserved and also that the container will be used with a properly configured dispenser housing. Alternatively, other embodiments are configured such that a particular container can be associated only with a particular dispenser housing and indicating device by way of a key device connected to that container.

The foregoing paragraphs have been provided by way of general introduction, and are not intended to limit the scope of the following claims. The various preferred embodiments, together with further advantages, will be best understood by reference to the following detailed description taken in conjunction with the accompanying drawings.

BRIEF DESCRIPTION OF THE DRAWINGS

FIG. 1 is a perspective view of a dispensing device including a dispensing housing with a viewing window revealing dosage indicia and a container positioned in an engaged position.

FIG. 2 is a perspective view of the dispensing device shown in FIG. 1 with the container in a first disengaged position.

FIG. 3 is an exploded perspective view of the dispenser housing, container, indicating device and connector shown in FIG. 1.

FIG. 4 is a perspective view of the dispensing device shown in FIG. 1 with the container in a second first disengaged position.

FIG. 5 is a top perspective view of the dispensing device shown in FIG. 4.

FIG. 6 is a perspective view of one embodiment of a mounting member portion of a connector.

FIG. 7 is a perspective view of one embodiment of an extension member.

FIG. 8 is an exploded perspective view of an alternative embodiment of a connector with the dispenser housing shown in partial cross-section.

FIG. 9 is an exploded perspective view of an alternative embodiment of a connector with the dispenser housing shown in partial cross-section.

FIG. 10 is an exploded perspective view of an alternative embodiment of a connector with the dispenser housing shown in partial cross-section.

FIG. 11 is a perspective view of a dispensing device including a dispensing housing, a container positioned in an engaged position and a hinged mouthpiece.

FIG. 12 is a perspective view of the dispensing device shown in FIG. 11 with the mouthpiece positioned in a cleaning position.

FIG. 13 is a cross-sectional perspective view of the dispensing device shown in FIG. 11.

FIG. 14 is a perspective view of one embodiment of the mouthpiece.

FIG. 15 is a perspective view of one embodiment of the dispenser housing.

FIG. 16 is an exploded perspective view of an alternative embodiment of a dispensing device including a dispenser housing, a container, an indicating device and a key device.

FIG. 17 is an enlarged, partial, perspective view of the indicating device and key device.

FIG. 18 is a bottom, exploded, perspective view of the indicating device, key device and container.

FIG. 19 is a perspective view of one embodiment of a first gear of the indicating device.

FIG. 20 is a perspective view of one embodiment of a second gear of the indicating device.

FIG. 21 is a perspective view of one embodiment of a ring of the key device.

FIG. 22 is a top perspective view of one embodiment of the indicating device without the first and second gears.

FIG. 23 is a partial, top perspective view of the indicating device shown in FIG. 22 without a top cover member and first and second gears.

FIG. 24 is a perspective view of an actuator member.

FIG. 25 is a side view of an alternative embodiment of a dispensing device with the container in a disengaged position.

FIG. 26 is a bottom perspective view of one embodiment of a tether cap member.

FIG. 27 is a side view of another embodiment of a tether cap member.

FIG. 28 is a partial, cut-way view of another embodiment of a tether cap member.

FIG. 29 is a top perspective view of another embodiment of a tether cap member.

FIG. 30 is a bottom perspective view of another embodiment of a tether cap member.

FIG. 31 is a side perspective view of another embodiment of a dispensing device with a cap member affixed thereto.

FIG. 32 is a partial cross-sectional cut-away view of the dispensing device shown in FIG. 31.

FIG. 33 is a side perspective view of another embodiment of a dispensing device.

FIG. 34 is a partial perspective view of the dispensing device shown in FIG. 33 with a top portion of the dispenser housing not shown.

FIG. 35 is a top perspective view of the bottom portion of the dispensing device shown in FIG. 33.

FIG. 36 is a partial side cut-away view of the top portion of the dispenser housing shown in FIG. 33.

FIG. 37 is a cross-sectional side view of another embodiment of a dispensing device.

FIG. 38 is a top view of the dispensing device shown in FIG. 37 with the container and connector not shown.

FIG. 39 is a top perspective view of the connector shown in FIG. 37.

FIG. 40 is an exploded side view of a dispensing device.

FIG. 41 is a partial, cut-away view of the dispensing device shown in FIG. 40 without the upper portion of the dispenser housing.

FIG. 42 is a partial, cut-away view of the dispensing device shown in FIG. 40 without the upper portion of the dispenser housing or the canister portion of the container.

FIG. 43 is a perspective view of the lower portion of the dispenser housing shown in FIG. 40.

FIG. 44 is a perspective view of an alternative embodiment of a dispenser housing lower portion.

FIG. 45 a partial view of a dispensing device incorporating the lower portion of FIG. 44 but without the upper portion of the dispenser housing or the canister portion of the container.

FIG. 46 is a partial, cut-away view of a dispensing device incorporating the lower portion shown in FIG. 44.

FIG. 47 is a partial, exploded perspective view of one embodiment of a dispensing device.

DETAILED DESCRIPTION OF THE PRESENTLY PREFERRED EMBODIMENTS

Referring to the drawings, and in particular FIGS. 1-5, a dispensing device, or dispenser, is shown as including a housing 10, or actuator boot, and a container 100 disposed therein. The housing has a longitudinally extending cavity 12 shaped to receive the container. A top portion of the housing is generally open such that the container can be inserted in the housing through opening 14 and be installed therein with a bottom end 102 of the container protruding from the housing and exposed to the user for actuation.

The term "longitudinal" as used herein is intended to indicate the direction of the reciprocal movement of the container relative to the housing. The terms "top," "bottom," "upwardly" and "downwardly" are intended to indicate directions when viewing the inhalation devices as shown in the Figures, but with the understanding that the container is inverted such that the top surface thereof is located adjacent the bottom of the housing and vice versa.

As shown in FIGS. 5, 13, 15, 41 and 46, a support block 16 having a well 18 is formed in a bottom portion 22 of the housing. An orifice 20 penetrates the support block to communicate with a bottom portion of the well. Referring to FIGS. 2-4, a mouthpiece 24, intended for insertion into the mouth of a patient, forms an exhaust port 26 that communicates with the orifice and well. The mouthpiece 24 extends laterally from the housing so as to facilitate insertion of the mouthpiece into the mouth of the patient.

The container 100 is formed as a cylindrical canister 104 having a 106 hub disposed on a top surface 108 thereof. The container also has a shoulder 180 and a neck portion 188. A valve stem 110 extends longitudinally from the hub. The valve stem extends coaxially from the canister and is biased outwardly therefrom by a spring (not shown) mounted within the canister. The container 100 is mounted in the housing by press fitting the valve stem 110 in the well 18 of the support block, which defines an "engaged" position of the container. The container is in a "disengaged" position when the valve stem 110 is removed from the well 18 of the support block.

It should be understood that the container can be configured in a variety of shapes and sizes, and that the substance contained therein can be released by any number of valve systems that are well known in the art. It should also be understood that the valve system can be actuated by a variety of actuators, including, but not limited to, various pumps, levers, actuator boots, buttons and the like. In such embodiments, the valve system can be actuated by an actuator moveable relative to the container and housing such that the container remains stationary relative to the housing.

In a preferred embodiment, the container 100 is filled with a substance which is dispensed therefrom in specific metered doses by depressing or moving the valve stem 110 from an extended closed position to a depressed open position, which in turn opens the value or value system. Preferably the substance is a medicament, although it should be understood that the container should be used to hold a variety of non-medicinal substances, including, but not limited to, various liquids, foams or aerosols. A single metered dose is dispensed from the container by each reciprocal, longitudinal movement of the valve stem and attendant opening and closing of the valve.

In operation, the opening of the valve stem and valve is effected by moving the container 100 reciprocally within the housing 10 along a longitudinal axis, defined by the valve stem and the reciprocal movement of the container, by depressing the exposed bottom end 102 of the canister relative to the housing 10 so as to move the valve stem 110 to the open position as it is supported within the well by the support block. Alternatively, an actuator can be moved to open the valve system of the container, which can remain stationary with respect to a supporting housing, a cap and/or an indicating device mounted thereto. For example, the actuator can be attached to the end of the container in the form of a pump device or the like.

As the valve stem is moved to the open position, the container dispenses a metered dose of the substance in aerosol form through the well 18 and orifice 20 and into the exhaust port. The substance in aerosol form is then transmitted to the user through the exhaust port of the mouthpiece by way of either a self-generated or assisted airflow. Alternatively, metered doses of liquids and the like can be dispensed from the container.

In other delivery systems, the housing and holder for the container are attached to a component having a chamber with an output end. Examples of these kinds of delivery systems are shown for example in U.S. Pat. No. 5,012,803, issued May 7, 1991, and U.S. Pat. No. 4,460,412, issued Sep. 11, 1984, the entire disclosures of which are hereby incorporated herein by reference. (No license, expressed or implied, is intended to be granted to either of these patents by reason of the incorporation by reference herein.) In these kinds of delivery systems, the component having the chamber can be adapted to receive the mouthpiece of the housing, or it can be integrally connected with a holder supporting the container. In either embodiment, the metered dose of substance, preferably a medicament, in aerosol is first dispensed from the container into the chamber, and thereafter inhaled by the user.

In a preferred embodiment, the container 100 is intended to dispense a predetermined number of metered doses of substance. For example, conventional inhaler containers typically hold on the order of 100 to 200 metered doses. In operation, it is important that the user be aware of the number of metered doses remaining in the container such that the user is not caught unaware with an empty canister when in need of the substance, such as a medicament.

Now referring to FIGS. 1-5, the dispenser is shown as including the housing 10, the container 100 mounted therein as described above and an indicator assembly 2. The indicator assembly can take many forms, as disclosed for example and without limitation in U.S. Pat. Nos. 6,142,339, 6,161,724, 6,435,372 and 6,561,384, the entire disclosures of which are hereby incorporated herein by reference. The indicator assembly can include a single indicator member, or a plurality of (i.e., more than one) indicator members, shown for example as three co-axially mounted indicator members 50 in the various embodiments of FIGS. 1-4, 16, 22, 23, 32, 34, 37, 40, 41 and 46. In addition, the indicator assembly can be configured as a mechanical device or an electrical device, or a combination thereof, and can include without limitation various analog and digital readouts and indicia.

Referring to FIGS. 3, 17, 22, 32 and 37, an actuator member 70 is configured as a post member 72 moveably supported in the housing along an axis parallel to the longitudinal axis defined by the reciprocal movement of the container within the housing. A spring 88 is disposed around the post and biases the actuator member upwardly against the top surface 108 of the canister, or against a mounting portion secured thereto. Although a compression spring is shown in the Figures, it should be understood that cantilever, torsion, leaf and tension springs, and the like, would also work to bias the actuator member upwardly into engagement with the container. The springs can be made of metal or plastic.

In operation, the container is moved longitudinally within the housing so as to depress the valve stem to the open position and thereby open the valve as explained above. As the container is moved downwardly within the housing, the actuator member 70 is moved longitudinally downward. When the container is released by the user, the spring (not shown) within the container biases the container upwardly within the housing along the longitudinal axis such that the valve stem 110 is moved to the closed position within the container so as to close the valve, while the spring biases the actuator member upwardly. As the actuator is reciprocally moved, it selectively engages a ratchet gear 72, which in turn operably moves one or more the indicator members upon a predetermined number of reciprocal movements.

The indicator members 50 are provided with indicia that are visible through one or more viewing windows 52. The indicia indicate to the user the number of doses that remain in or have been dispensed from the container. In one embodiment, the indicia take the form of a color code, where, for example, a portion of the wheel is colored green to indicate the starting full position, a portion is colored yellow to indicate a medium fullness and a portion is colored red to indicate that the container is empty. Obviously, other colors, shading or alpha-numerical indicia can be provided on the indicator wheel to indicate the relative fullness or emptiness of the container.

In one embodiment, the indicator assembly includes three indicator members 50 coaxially mounted on an axle 56 and rotatable thereabout. Each of the indicator members is configured as an indicator wheel having a circumferential skirt with an outer circumferential surface 60 on which indicia (shown as numbers) are applied. In this embodiment, the ratchet gear 72 is coaxially mounted with the indicator wheel. The ratchet gear 72 includes a plurality of teeth formed around its periphery. In one embodiment, the ratchet gear is integrally molded with the indicator wheel, although it should be understood that the gear and wheel can be made separately and thereafter attached one to the other by welding, adhesive and the like.

In one embodiment, the first indicator member includes a resilient advancement member 62 that overlies the ratchet gear teeth of the second indicator member. Likewise, the second indicator member includes an advancement member that overlies the ratchet gear teeth of the third indicator member. It should be understood by one of skill in the art that one or more indicator members may be used to provide an indication of dosages used or available, and that the three indicator members shown in the Figures is meant to be illustrative, rather than limiting. In addition, it should be understood that a plurality of indicator members refers to any number of indicator members greater than one.

Referring to FIG. 38, a housing 10 is shown as having a pair of engagement members 64 formed integrally with the housing and including ramped surfaces. A plurality of non-return members 66 extend from the housing and selectively engage the ratchet gear to ensure unidirectional rotation of the indicator member. Although the engagement members and non-return members are shown as being formed in or extending from a module housing, shown in FIGS. 3 and 16 and as described below, one of skill in the art should understand that those members or equivalent features could also be formed in or connected to the dispenser housing or actuator boot that supports the container as shown in FIGS. 34, 37 and 38 or disposed on or connected to the container itself.

In operation, the container is moved longitudinally within the housing 10 so as to depress the valve stem 110 to the open position so as to open the valve as explained above. As the container is reciprocally moved within the housing, the actuator 70 engages the ratchet gear 72 secured to the first indicator member and rotates the first indicator member a predetermined angular or incremented amount corresponding to the pitch of the teeth disposed around the periphery of the ratchet gear.

The reciprocal movement of the container relative to the housing is repeated until the first indicator member 50, and its ratchet gear 72, are rotated one complete revolution. The predetermined number of reciprocal movements required to advance the first indicator member one revolution is equal to the number of teeth disposed about the periphery of the ratchet gear 72. As the first indicator member is rotated by successive movements of the container relative to the housing, the advancement member 62 of the first indicator member is brought into selective engagement with the engagement member 64, configured with the ramped surface formed in the housing. In particular, the engagement member 64 biases a tooth portion of the advancement member 62 into engagement with one of the teeth of the ratchet gear 72 on the second indicator member.

As the first indicator member is further rotated by successive movements of the container relative to the housing, whether it be the dispenser housing for the container or the module housing described below, the advancement member 62 engages one of the teeth on the ratchet gear 72 of the adjacent (i.e., second) indicator member and advances the indicator member a predetermined incremental angular amount corresponding to the pitch of the ratchet gear teeth. The term incremental is meant to refer to the angular amount the indicator member is moved by the advancement of one actuation, which corresponds to the movement of one tooth, regardless of whether the indicating device is indicating the number of doses left (e.g., counting down) or indicating the number of doses administered (e.g., counting up).

As the resilient advancement member 62 clears the engagement member 64, it springs away from the ratchet gear such that further advancements of the first indicator member do not effect a rotation of the second indicator member until the first indicator member completes yet another cycle so as to again bring the advancement member into engagement with the next tooth of the second indicator member ratchet gear, and so on. The second indicator member with its advancement member similarly interacts with a second engagement member overlying the teeth of the third indicator member so as to selectively engage and advance the third indicator member a predetermined incremental amount for each complete rotation of the second indicator member. It should be understood that more indicator members could be similarly assembled to provide an incremental indicating device.

Referring to FIGS. 40, 41 and 46, a secondary or warning indicator member 300 is rotatably supported in the dispenser housing adjacent the indicator members about an axis parallel to and spaced apart from the axis of the indicator members 50. The warning indicator 300 has an outer circumferential surface with warning dosage indicia applied thereto. Preferably, the warning dosage indicia takes the form of a color coding, for example a portion or zone of the surface is green, while another portion or zone is red. Preferably a plurality of zones is used, for example and without limitation two zones of green and red respectively, or three zones of green, yellow and red. Alternatively, alphanumeric characters, text messages etc. as herein described can be used as indicia. It should be understood that a surface of the indicator member perpendicular to the axis of rotation also can be configured with the indicia. The surface of the indicator member is visible through a viewing window 302 formed in the dispenser housing.

The second indicator member 300 further includes at least one driven member 306, and preferably a plurality of driven members, configured in one embodiment as a teeth extending radially outward from the second indicator member on one side of the circumferential indicia surface. Taking into account the spacing between the axes of rotation for the first and second indicator members 50, 300, a drive member coupled to one of the indicator members and the driven members are configured and have sufficient lengths so as to mesh after a predetermined number of rotations of the first indicator member 50 configured with the drive member. The second indicator member 300 is also provided with a plurality of ratchet teeth 308 formed circumferentially around the axis of rotation on the side of the indicator member opposite the drive member. A non-return member extends from the dispenser housing or module housing and successively, selectively engages one or more of the ratchet teeth 308 so as to allow the second indicator member 300 to rotate in only one direction. Various embodiments incorporating a warning indicator are further disclosed in U.S. patent application Ser. No. 10/968,815, filed Oct. 18, 2004 and entitled Indicating Device With Warning Dosage Indicator, the entire disclosure of which is hereby incorporated herein by reference.

In a preferred embodiment of the dispenser, shown in FIGS. 3 and 16-18, the indicator assembly is arranged in an indicator module 90. The indicator module 90 is shaped to be received within the housing where it is disposed around a portion of the support block 16. In particular, the support block is spaced apart from the wall of the dispenser housing, otherwise referred to as the actuator boot, so as to form a donut-shaped socket in the bottom of the housing. The module includes a module housing 92 having an inner concave surface that is shaped to mate with an outer convex surface of the cylindrical support block and an outer convex surface that is shaped to mate with the inner concave surface of the housing which is also generally cylindrical. In this way, the module housing is shaped to be received within the socket formed around the support block. Preferably, the module housing has a semicircular shape and fits around a portion of the support block opposite the orifice opening so as to not interfere with the dispensing of the medicament, or the airflow transmitting the medicament to the patient. In this way, the module is maintained rearwardly of the midpoint of the support block. One of skill in the art should understand, however, that the module, or module housing, can be configured in any number of different sizes and shapes so as to be accommodated in a variety of housings or cap assemblies, with or without support blocks and the like. The module housing can be made of a single piece, or from two or more pieces joined to form the housing.

It should be understood, however, that the module can be secured within the housing by any number of conventional means, including the use of fasteners or adhesive. Alternatively, the module can simply be press fit into the socket formed between the support block and housing wall.

In various embodiments, as explained above, the indicia are applied to a circumferential surface 60 of the indicator wheel, for example in the form of numbers ranging from 0 to 9, with the ratchet gear on the indicator member having 10 teeth. In operation, it should be understood that the three, or more or less, indicator members can be preset to the maximum number of dosages contained within the container, with the indicia, or in this case numbers, arranged about the periphery of the indicator wheel, such that successive, sequential actuations of the container cause the indicator members to count down.

Alternatively, the indicator members are assembled such that the zero (0) of each indicator member is displayed in the viewing window to the user. The container is then actuated by the user such that the first indicator member rotates within the housing to sequentially display the number of doses that have been dispensed from 1 to 9. Upon the tenth actuation, the indicator member completes a single revolution, by virtue of the ten teeth preferably formed about the ratchet gear which correspond to the predetermined number of actuations, and causes the second indicator member to advance one number from 0 to 1 as the first indicator member again displays a 0 such that the two members together indicate that 10 dosages have been dispensed. The first indicator member is again rotated by successive actuations until another single rotation is completed to further rotate the second indicator to reveal the 2, so as to indicate that 20 dosages have been dispensed. Upon a complete rotation of the second indicator member, corresponding to 100 actuations, the third indicator member is advanced to reveal a 1 in the viewing window with the first and second indicator members revealing a 0, and so on.

Although the indicator assembly embodiments of FIGS. 1-5, for example, are shown as being mounted in the indicator module, one of skill in the art should understand that the assembly, including the axle, indicator members, ratchet gears, actuator member and spring could be mounted directly in the dispenser housing or actuator boot that supports the container, as shown for example in FIGS. 34, 41 and 46. Similarly, the engagement member, or members, and non-return member, or members, could be formed in the dispenser housing that supports the container, otherwise referred to as the actuator boot, as shown in FIG. 38.

Referring to the embodiments of FIGS. 1-7, a connector 4 connects the container and the dispenser housing, and maintains the connection therebetween as the container is moved between the engaged and disengaged positions. The term "connected" as used herein means that two or more members or components are coupled, whether directly or indirectly, for example with an intervening member or component. For example, it should be understood that the container is connected to the dispenser housing when it is connected to the indicator assembly, which in turn is connected to the dispenser housing. The term "fixedly connected," or variations thereof, means that one component connected to another is not meant to be disconnected during the normal operation of the device and without undue force, while "releasably connected," means that one component is meant to be disconnected during such normal operation and without undue force.

In one embodiment, the connector includes mounting portion 30 mounted to the container. The mounting portion, shown in FIG. 6, includes a locking ring or collar 32 that is engaged with the hub 106, for example by snap-fit, and an annular wall that surrounds the end portion of the container. The mounting portion can include a longitudinal slit to allow the collar to be snap fit onto the container. The mounting portion includes a pair of follower members 34 extending from the annular wall on opposite sides thereof. Each follower member includes a stem 36 and cap portion 38.

The connector further includes a pair of longitudinally extending guide portions 40 formed along an interior of the dispenser housing. Each guide defines a track 42. The guides include a top portion 44 that extends longitudinally from the top of the dispenser housing. The track 42 terminates at an upper portion of the guide 44 to define a travel limiting stop 46.

In one embodiment, shown in FIGS. 11-15, the follower members 34 formed on the mounting portion are directly mounted in the track 42, with the head or cap portions 38 being retained by the guide 40, such that the container can be translated relative to the guide in the track between the engaged and disengaged positions. At the uppermost position of the container relative to the dispenser housing, and depending on the length of the top portions 44 of the guide, the container can also be rotated relative to the dispenser housing about an axis 48 defined by the follower members so as to provide access to the interior of the dispenser housing 10.

Alternatively, or in addition thereto, the mouthpiece 24 is rotatably connected to an upper portion 6 of the dispenser housing. In one embodiment, the upper portion, which also includes the support block 16, includes a pair of axles 8 extending laterally outward from an exterior thereof. In addition, the housing includes a catch component 54 formed along a top of a mouthpiece opening 78. The mouthpiece includes a pair of tabs 74 defining openings 76 or sockets shaped to receive the axles 8. The mouthpiece further includes a catch component 58, that releasably engages the catch component 54 on the upper housing portion to releasably secure the mouthpiece in a closed, operable dispenser condition. The mouthpiece can be rotated or pivoted about an axis 80 defined by the axles to a cleaning position, wherein the user is provided with access to the interior of the upper portion of the dispenser housing, including the support block.

In another embodiment, shown in FIGS. 1-7, the connector further includes a pair of extension members 82. Each extension member has a follower member 86 protruding laterally therefrom and a longitudinal track 84, having terminal upper and lower ends 94, 96 defining travel limiting stop portions. The follower members 34 on the mounting portion are mounted in the tracks 84 of the extension members respectively and translate relative thereto. In addition, the follower members 34 can be rotated about the axis 38 relative to the extension members. At the same time, the extension members 82 can be translated by moving the follower members 86 thereof in the tracks 42 formed in the dispenser housing. The extension members 82 can also be rotated relative to the dispenser housing, as shown in FIGS. 4 and 5, by rotating the extension members about an axis 98 defined by the follower members 86 thereof.

In operation, the container 100 is moved from the engaged to the disengaged position. As the container is translated out of the dispenser housing, as shown in FIG. 2, the container 100 translates relative to the extension member 82, while the extension member translates relative to the dispenser housing 10 after the mounting portion follower members 34 are engaged with the top travel limiting stop portion 96. As the container is completely removed from the dispenser housing, the container 100 can be rotated relative to the dispenser housing 10 and the extension members 82. Likewise, once the extension members are fully translated relative to the dispenser housing such that the follower members 86 are engaged with the upper travel limiting stop portion 46, the extension member 82 can also be rotated relative to the dispenser housing 10. In this way, the container can be translated and rotated, or moved, so as to provide access to the cavity 12 of the dispenser housing, for example to clean the housing, while maintaining a connection between the container and the dispenser housing.

In an alternative embodiment, shown in FIG. 8, the mounting portion 130 includes a wall portion that extends longitudinally along the side of the container. The mounting portion forms a pair of guides each having a track 132. In turn, a pair of follower members 134 extend laterally inward from an interior surface of the dispenser housing and are engaged in the tracks. In operation, the container and mounting portion, which is attached to the container, are translated relative to the follower members 134 and dispenser housing 10. In one embodiment (not shown), the follower members are formed on an extension portion of the dispenser housing that extends from the top thereof such that the container and mounting portion can also be rotated relative to the dispenser housing.

In another embodiment, shown in FIG. 10, the extension member 82 of FIG. 7 is incorporated into the embodiment of FIG. 8, but with the follower member 86 of the extension members engaged in the tracks 132 of the mounting portion and the follower members 134 of the dispenser housing engaged in the tracks 84 of the extension members. During operation, the container and mounting portion 130 can be translated and/or rotated relative to the extension members 82 while the extension members can be translated and rotated relative to the dispenser housing 10.

In yet another embodiment shown in FIG. 9, the dispenser housing includes a pair of guides 40 each defining a track 42. A pair of extension members 182 each include a pair of longitudinally spaced follower members 184, 186 extending from opposite sides of the extension member on opposite ends thereof. The follower members 184, 186 are engaged respectively with the tracks 132, 42 formed on the mounting portion and dispenser housing to allow the container and mounting portion to be translated and rotated relative to the extension member and dispenser housing, and also to allow the extension member 182 to be translated and rotated relative to the dispenser housing 10, such that the container can be completely removed from the dispenser housing, but remain connected thereto.

It should be understood that although a pair of extension members, tracks, guides, follower members etc. are shown, that one or more than two such members can also be used to connect the container and the dispenser housing.

The various embodiments of FIGS. 1-15 maintain the connection between the container 100 and dispenser housing 10 so as to avoid a count corruption of the indicating device relative to the container, but also permit the container to be moved to a disengaged position so as to allow the dispenser housing to be cleaned.

In another embodiment, shown in FIGS. 37-39, a mounting portion 112 includes a plurality (shown as three) longitudinally extending arms 114 each having a catch portion 120 formed on a free end thereof. A collar portion 116 of the mounting portion includes longitudinal slits 122, allowing the collar portion to be snap fitted around the neck 188 of the container.

The dispenser housing includes a corresponding plurality of guides 118 each defining an opening or track. The arms 114 are disposed through the guides 118 such that the catch portions 120 engage a bottom of the guides and prevent the container from being removed therefrom when moved to a disengaged position. Alternatively, the catch portions 120 engage the bottom of the guides 118 as the container is moved to the engaged condition and thereafter maintains the container in the engaged position, thereby precluding it from being moving to the disengaged position. The arms 114 move relative to the guides 118 as the container 100 is reciprocally moved relative to the support block 16. In this embodiment, the indicator assembly is mounted directly in the bottom of the dispenser housing, although it should be understood that a module housing could also be used.

For example, and referring to the embodiment of FIG. 47, the arms 114 and catch portions 120 are inserted through openings 91 formed in the top of a module housing 90 and defining guides. The catch portions 120 engage a bottom of the top wall of the housing and prevent the container from being disengaged from the module housing 90 when the container is moved to a disengaged position. Alternatively, the catch portions 120 engage the module housing 90 as the container is moved to the engaged condition and thereafter maintains the container in the engaged position, thereby precluding it from being moving to the disengaged position. The arms 114 move relative to the openings 91 and module housing 90 as the container 100 is reciprocally moved relative to the support block 16. The module housing 90 can be fixedly secured to the dispenser housing, for example by snap-fit engagement with one or more tabs 93 that engage, for example and without limitation, a front, vertical surface and a top surface of the module housing 90. The module housing can also be attached by friction fit, welding (e.g., sonic), with adhesives, or some combination of the above.

In this way, in some embodiments, the dispenser housing 10 does not need to be modified or otherwise altered from a configuration wherein a dose indicator is not used. Rather, the user simply secures the module housing 90 in the bottom of the dispenser housing 10, for example with adhesives or friction fit, and thereafter secures the container 100 to the module housing 90, for example with the arms 114.

Referring to the embodiment of FIGS. 33-36, the indicating device is mounted in a bottom portion 124 of the dispenser housing, either directly or with a module housing. An upper portion 126 of the dispenser housing is connected to the bottom portion. It should be understood that the bottom and upper portions can be made as separate members, which are affixed to one another for example with mechanical fasteners (e.g., snap fit), adhesives, ultrasonic welding or the like. The upper portion includes a plurality of downwardly inclined lugs 128 or arms that snap fit around the container 100 as the neck of the container is slid past the lugs and as the valve stem 110 is inserted into the support block 16, with the lugs engaging the shoulder 180 of the container. The lugs, or catch portions, can be spaced from the support block such that they maintain the container in an engaged position at all times, or they can be spaced upwardly such that the container can be moved to a disengaged position, but cannot be removed from the dispenser housing. The catch portions engages the ferrule portion of the container to prevent it from being disengaged from the dispenser housing, while allowing the container to move downwardly relative to the catch portions to dispense a dose of substance.

Referring to the embodiment of FIGS. 44-46, the lugs or arms 128, i.e. catch portions, can be formed in the lower portion 124, which can include an integrally formed mouthpiece, or can have a separate mouthpiece 24 rotatably or pivotally connected thereto. The lugs 128 function in the same way as described above, but in this embodiment permit the removal of the upper portion 126 of the dispenser housing, for example to permit cleaning of the device. One of the upper or lower portions can be configured with a stepped in wall 214 and shoulder 216, which receives the other portion by way of a friction fit. Alternatively, one or the other of the upper and lower portion can be provided with one or more bumps or protuberances to frictionally or snap-fittingly engage the other component.

Referring to FIGS. 40-43, the dispenser housing includes a lower or bottom portion 124, an upper portion 126 and a mouthpiece 24 rotatably connected to the lower portion 124. In another embodiment, the mouthpiece is formed integrally with the lower portion 124. In one embodiment, the upper portion 126 is made of a clear plastic, or is otherwise see-through, such that the user can view the container, for example to read a label or prescription applied thereto. The entirety of the upper portion can be made see-through, or it can be provided with a see-through viewing window permitting viewing of a portion of the container, with the remainder of the upper portion not being see-through. The see-through aspect of the upper portion can be important, for example, if the upper portion and container are fixed to the lower portion such that they are not removeable therefrom, for example to permit viewing of the label affixed to the container. Of course, the lower portion and mouthpiece can also be made see-through.

In one embodiment, the upper portion 126 is removably attached to the lower portion 124 to facilitate cleaning of the device. For example, one of the upper or lower portions can be configured with a stepped in wall 214 and shoulder 216, which receives the other portion by way of a friction fit. Alternatively, one or the other of the upper and lower portion can be provided with one or more bumps or protuberances to frictionally or snap-fittingly engage the other component.

A locking ring 202 is secured in the lower portion, for example and without limitation by friction fit, snap fit, welding, adhesives and/or some combination thereof. The ring has a central opening 204 formed by a scalloped inner periphery 206 defined by a circular opening 208 having a plurality (shown as six) of semi-circular openings 210 spaced around the periphery of the circular opening. The combination of openings forms a plurality (shown as six) of gripping tabs 212 or catch portions. The tabs 212 engage the container, and in particular surround the neck 188 thereof, with a snap-fit, such that the container is maintained in an engaged position with the support block, but cannot be disengaged from the lower portion by way of the locking ring 202 engaging the shoulder

180 of the container. The circulatory openings 210 or cut-outs permit air flow past or through the ring during actuation of the container. It should be understood that more or less openings could be formed. Alternatively, the ring can be formed with a single, central circular opening to receive the container, with other openings formed through the ring and spaced from the central opening if necessary to permit air flow.

Referring to FIGS. 31 and 32, another embodiment of a dispensing device includes a cap member 136 formed from a resilient, flexible material, such as rubber. The cap is secured over the container once it is positioned in the engaged position. The cap can be fixedly secured to the dispenser housing with adhesives, fasteners and the like. The user actuates the container by pushing on the rubber cap, which deforms as the container moves longitudinally downward relative to the dispenser housing. The dispenser housing is provided with a plurality of vent holes 138 that allow air to escape when the cap member is depressed to actuate the container.

It should be understood that the embodiments of FIGS. 31-46 can be configured so as to maintain the container in the engaged position once it is installed in the dispenser housing, meaning that it cannot be moved to the disengaged position with the valve stem removed from the support block. In this way, a single container is associated with a corresponding indicating device such that the count of dosages cannot be corrupted by removing the container from the dispenser housing and using it with a different housing. At the same time, the mounting arrangement permits the container to reciprocally move in the longitudinal direction relative to the support block so as to allow dosages of substance to be dispensed.

Referring to FIGS. 25-30, another embodiment of a dispensing device includes a connector including a tether 140. A cap member 142, or other mounting portion, includes an anchor 144. The cap member 142 is mounted to the container, either fixedly or releasably. In one embodiment, shown in FIG. 26, the cap member 142 includes a plurality of interior radially extending ribs 148 that engage the end of the container with a friction fit. In another embodiment, shown in FIG. 27, the cap member 142 includes a plurality of resilient tabs or fingers 150, which act as engagement members to engage the container.

Referring to FIG. 28, the cap member 242 is formed in a disc shape, with a bottom of the cap being attached to the bottom of the container with adhesives, or other suitable attachment devices. On the top of the cap, an anchor 144 is provided for connection to one end of the tether 140.

Referring to FIG. 29, the cap member 242 has a key hole formed therein and defining an anchor, with the key hole including a slot 244 and a hole 246 formed in a bottom of the cap member. The tether 140 includes a knot or stop portion formed on an end thereof which extends through the hole 246 in an engaged configuration, while the tether lies in the slot and extends from the cap member through an opening 248 in the side thereof defined by the slot. The opposite end of tether is secured to an anchor on the dispenser housing as explained below.

Referring to FIG. 30, the cap member 142 includes a slot 244 opening to the side thereof at an opening 248 such that the tether lies in the slot between the cap member and the bottom of the container and extends through the slot. The cap member further includes a hole 246 configured to secure an enlarged end of the tether.

The dispenser housing includes an anchor 146, which can be located on the exterior or interior of the housing. In one embodiment, the tether is made of a stretchable material, such as an elastomeric material, e.g. rubber or silicone. In other embodiments, the tether is made of a non-extensible material, which may or may not be contained in a retraction mechanism that winds and stores the tether. Opposite ends of the tether 140 are secured to the anchors 144, 146.

In operation, the user moves the container 100 from an engaged position to a disengaged position, which can include removing the entire container from the dispenser housing, for example to clean the housing. At the same time, the tether maintains the connection of the container with the dispenser housing such that the dosage count is not corrupted.

Referring to the embodiment of FIGS. 17-24, a dispenser device includes a dispenser housing 10, a key device 152 and an indicating device 90. The key device 152 has a mounting portion 158 connected to the container, for example by snap fit to the hub or neck of the container. IN one embodiment, the mounting portion 158 includes a collar 32 as disclosed above with respect to FIG. 6.

Referring to FIGS. 17-24, the key device 152 further includes first and second rotatable rings 154, 156, shown for example in FIG. 21, which are rotatably secured to the mounting portion with the first ring disposed circumferentially around the second ring. In one embodiment, the mounting portion includes an edge portion on the bottom thereof that supports the rings. Each ring 154, 156 includes an opening 160, 162, or key passageway, formed in a bottom surface thereof. In an alternative embodiment, one or both of the rings includes a key portion extending downwardly therefrom. The key portion can be configured as a triangular tab member for example and without limitation.

The indicating device is connected to the dispenser housing as explained above. The indicating device further includes first and second gears 164, 166 rotatably mounted to the top thereof, e.g. sit in the base housing, and are rotatable about the longitudinal axis. The first and second gears include first and second key portions 168, 170 extending upwardly therefrom. It should be understood that one or both of the first and second gears could also be configured with a key passageway. The key portions 168, 170 are disposed in the key passageways 160, 162 as the container is moved to an engaged position with the valve stem engaged with the dispenser housing. Initially, the key passageways and key portions are aligned, for example side by side. When the container is moved to the disengaged position, the first and second key portions are removed from said first and second key passageways respectively.

Each of the first and second gears 164, 166 includes a plurality of gear teeth extending from a bottom thereof and arranged circumferentially around the gears. The teeth of the outer, first gear 164 are engaged with a drive gear 172 rotatably mounted in the module housing, as shown in FIG. 23. The drive gear is coaxially mounted with a ratchet gear 174. The actuator 70, shown in FIG. 24, includes a finger or tab member 176 that selectively engages the teeth of the ratchet gear 174 and rotates the gear an incremental amount upon each reciprocal movement of the actuator 70 and container 100. In turn, the drive gear 172 rotates with the ratchet gear 174 and thereby rotates the outer gear 164 an incremental amount. The key portion 168 engages the ring 154 in the key passageway 160 and moves the ring on the container mounting portion.

Upon one complete revolution of the outer gear 164, an advancement member 178 extending radially and circumferentially along the inside of the outer gear, is biased inwardly by an engagement member formed on the indicator housing 92 into engagement with one of the teeth formed on the inside gear 166 so as to advance the inside gear 166. The inside gear 166 in turn rotates the second ring 156 by way of engagement of the key portion 170 with the key passageway 162.

In operation, the user reciprocally moves the container 100 relative to the valve stem 110 and dispenses a dosage of substance from the container upon each reciprocal movement of the canister. The first gear 164 is rotated by the drive gear 172 a first incremental amount in response to each reciprocal movement of the canister, and selectively engages the second gear 166 with the first gear upon a predetermined number of reciprocal movements of the canister. The first gear rotates the second gear a second incremental amount. As the first and second gears, and corresponding first and second rings, are moved to different positions, they define a changing unique key pattern corresponding to the number of doses that have been dispensed. Accordingly, only a container that has had the same number of doses dispensed therefrom can be reengaged with the dispenser housing, since the key portions 168, 170 must mate with the key passageways 160, 162 before the valve stem can be engaged with the support block.

In one embodiment, the container 100 is configured with a unique indicia that matches a corresponding unique indicia located on the housing 10, the indicating device or assembly, or a combination of the housing and indicating device. For example, the container and housing can be configured with a matching color or alpha numeric character, or a combination of both, such that the user is advised that a particular container is associated with a particular housing. For example and without limitation, both the container and housing can be configured with a label having a particular color (e.g., red) and an alpha-numeric indicia, e.g., "B263." In this way, the user is advised that the container matches the dispenser and is assured that the count indication on the indicating device associated with that dispenser corresponds to that container. In this way, there is additional assurance of the number of doses remaining in the container, or the number of doses already dispensed therefrom. This identification system can be used by itself, i.e. as a primary linking/identification tool, or as an auxiliary identification tool used in cooperation with the other embodiments and connector devices disclosed herein.

In one embodiment, each container and corresponding housing/indicating device is provided with a unique indicia that is not duplicative of indicia used with any other housing/indicating device. In another embodiment, the indicia may be reused after the passage of time, for example a certain time beyond the expiration of any particular lot of medicament, such that an infinite number of indicia is not required. In yet another embodiment, containers and housings/indicating devices dispensed to a particular user are configured with unique indicia, for example by having the pharmacy or other retailer maintaining records and assigning new indicia to refills and new prescriptions so as to preserve the uniqueness relative to that particular user. In this embodiment, other users may randomly be assigned the same indicia as the indicia used by a particular user, but the uniqueness is preserved for each user.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. A system of medicament dispensers comprising:
   a plurality of dispenser housings each having a unique first indicia different from said first indicia of the other of said plurality of dispenser housings, wherein said unique first indicia is capable of being seen by a user, and wherein each of said plurality of dispenser housings is configured with a dosage indicating device; and
   a plurality of containers each holding dosages of the same type of medicament, each of said containers having a unique second indicia different from said second indicia of the other of said plurality of containers, wherein said unique second indicia is capable of being seen by the user, and wherein said unique second indicia of each of said containers corresponds to one of said unique first indicia of a corresponding one of said plurality of dispenser housings, wherein each of said containers is coupled to said corresponding one of said dispenser housings.

2. The system of claim 1 wherein each of said plurality of dispenser housings is configured with a well and each of said plurality of containers is configured with a valve stem, wherein said valve stem of each of said containers is shaped to be removeably received in said well of said corresponding one of said plurality of dispenser housings.

3. The system of claim 1 wherein each of said plurality of first indicia and each of said plurality of second indicia comprises alphanumeric characters.

4. The system of claim 3 wherein each of said plurality of said first indicia comprises a color.

5. The system of claim 1 wherein each of said first indicia are applied to a corresponding dispenser housing with a label.

6. The system of claim 1 wherein each of said second indicia are applied to a corresponding container with a label.

7. The system of claim 1 wherein said pluralities of unique first and second indicia are associated with a single, particular user.

8. The system of claim 1 wherein the uniqueness of said pluralities of unique first and second indicia are preserved for a certain time period.

9. The system of claim 8 wherein said time period extends beyond an expiration of a particular lot of said medicament.

10. The system of claim 1 wherein each of said plurality of dispenser housings is configured with a mouthpiece.

11. A medicament dispenser comprising:
    a dispenser housing having a unique first indicia, wherein said unique first indicia is non duplicative of indicia used with any other dispenser housing prescribed for a particular user;
    a container holding dosages of a medicament, said container having a unique second indicia corresponding to said unique first indicia, wherein said unique second indicia is non duplicative of indicia used with any other container prescribed for the particular user; and
    wherein said dispenser housing is configured with a dosage indicating device capable of indicating the number of dosages of medicament dispensed from or remaining in the container.

12. The medicament dispenser of claim 11 wherein said unique first and second indicia each comprise alphanumeric characters.

13. The medicament dispenser of claim 11 wherein said unique first and second indicia each comprise a color.

14. The medicament dispenser of claim 11 wherein said unique first and second indicia are identical.

15. The medicament dispenser of claim 11 wherein said dispenser housing is configured with a first label comprising said first indicia.

16. The medicament dispenser of claim 15 wherein said container is configured with a second label comprising said second indicia.

17. The medicament dispenser of claim 11 further comprising a connector coupled between said dispenser housing and said container.

18. The medicament dispenser of claim 17 wherein said connector comprises a tether.

19. A kit adapted for assembly into a medicament dispenser comprising:
- a dispenser housing;
- a container holding a plurality of dosages of medicament, said container capable of being associated with said dispenser housing for dispensing dosages of medicament from said container;
- a dosage indicating device capable of being associated with said dispenser housing for indicating the number of dosages of medicament dispensed from or remaining in said container;
- a first label capable of being associated with said dispenser housing, said first label comprising a unique first indicia, wherein said unique first indicia is non duplicative of indicia used with any other dispenser housing prescribed for a particular user; and
- a second label capable of being associated with said container, said second label comprising a unique second indicia, wherein said first and second indicia are matching, wherein said unique second indicia is non duplicative of indicia used with any other container prescribed for the particular user.

20. The kit of claim 19 wherein said first and second matching indicia are identical.

21. The kit of claim 20 wherein said first and second indicia each comprise alphanumeric characters.

22. The kit of claim 20 wherein said first and second indicia each comprise a color.

23. The kit of claim 19 wherein said first and second labels comprise a first pair of labels, and further comprising a plurality of other pairs of labels, wherein each of said pairs of labels comprises different matching first and second indicia.

24. A method for assembling a medicament dispenser comprising:
- providing a dispenser housing comprising a dosage indicating device;
- providing a container holding a plurality of dosages of medicament;
- applying a first label to said dispenser housing, said first label comprising a unique first indicia, wherein said unique first indicia is non duplicative of indicia used with any other dispenser housing prescribed for a particular user;
- applying a second label to said container, said second label comprising a unique second indicia, wherein said first and second indicia are matching, wherein said unique second indicia is non duplicative of indicia used with any other container prescribed for the particular user; and
- connecting said container to said dispenser housing.

25. The method of claim 24 wherein said connecting said container to said dispenser housing comprises inserting a valve stem of said container into a well of said dispenser housing.

26. The method of claim 24 wherein said first and second indicia are identical.

27. The method of claim 24 wherein said first and second indicia each comprise alphanumeric characters.

28. The method of claim 24 wherein said first and second indicia each comprise a color.

29. The method of claim 24 further comprising providing a second dispenser housing comprising a second dosage indicating device; providing a second container holding a second plurality of dosages of said medicament; applying a third label to said second dispenser housing, said third label comprising a unique third indicia; and applying a fourth label to said second container, said fourth label comprising a unique fourth indicia, wherein said third and fourth indicia are matching, and wherein said third and fourth indicia are different than said first and second indicia; and connecting said second container to said second dispenser housing.

30. The method of claim 29 further comprising providing a plurality of subsequent dispenser housings each comprising a dosage indicating device; providing a plurality of subsequent containers each holding a plurality of dosages of said medicament; applying pairs of labels to corresponding subsequent dispenser housings and containers, wherein said pairs of labels each comprise matching indicia, and wherein said matching indicia of each of said pairs of labels is different than said matching indicia of the other pairs of labels.

* * * * *